US006200576B1

(12) United States Patent
Hwong et al.

(10) Patent No.: US 6,200,576 B1
(45) Date of Patent: Mar. 13, 2001

(54) SWINE VESICULAR DISEASE VIRUS AND MUTANT STRAINS AND PREPARATION PROCESS AND USE THEREOF

(75) Inventors: Ching Long Hwong; Cheng-Kai Lo; Ying-Chuan Yang; King-Song Jeng; Edward L. Chang, all of Taipei (TW)

(73) Assignee: Development Center for Biotechnology, Taipei (TW)

( * ) Notice: Subject to any disclaimer, the term of this patent is extended or adjusted under 35 U.S.C. 154(b) by 0 days.

(21) Appl. No.: 09/116,032

(22) Filed: Jul. 15, 1998

(51) Int. Cl.$^7$ .......................... A61K 39/125; C12N 7/00; C12N 15/41

(52) U.S. Cl. ..................... 424/216.1; 424/186.1; 424/815; 435/235.1; 435/320.1; 536/23.72

(58) Field of Search ...................... 536/23.72; 435/235.1, 435/236, 5, 320.1; 424/216.1, 815, 186.1

(56) References Cited

U.S. PATENT DOCUMENTS 5,478,746 * 12/1995 Cohen et al. ...................... 536/23.72

OTHER PUBLICATIONS

Hagan and Bruner's Microbiology and Infectious Diseases of Domestic Animals, Eighth Edition. Ed. J.F. Timoney et al, Comstock Publishing Associates, Ithaca, NY, pp. 674–676, 1988.*

Veterinary Virology, Second Edition. Ed. F.J. Fenner, Academic Press, Inc., San Diego CA, pp. 412 and 417–428, 1993.*

"Technical Bulletin"; *Promega*; 1994; No. 206, pp. 1–8.

Vincent R. Racaniello and David Baltimore; "Cloned Poliovirus Complementary DNA is Infectious in Mammalian Cells"; *Science*; 1981; vol. 214, pp. 916–919.

Toru Inoue, Taiko Suzuki and Kiichi Sekiguchi; "The Complete Nucleotide Sequence of Swine Vesicular Disease Virus"; *J. gen. Virol.*; 1989; pp. 919–934.

Steffan N. Ho, Henry D. Hunt, Robert M. Horton, Jeffrey K. Pullen and Larry R. Pease; "Site–directed mutagenesis by overlap extension using the polymerase chain reaction"; *Gene*; 1989; pp. 51–59.

P. Seechurn, N.J. Knowles and J.W. McCauley; "The complete nucleotide sequence of a pathogenic swine vesicular disease virus"; *Virus Research*; 1990; vol. 16, pp. 255–273.

Toru Inoue, Shigeo Yamaguchi, Takakiyo Saeki and Kiichi Sekigushi; "Production of infectious swine vesicular disease virus from cloned cDNA in mammalian cells"; *Journal of General Virology*; 1990; vol. 71, pp. 1835–1838.

Toru Inoue et al.; "The complete nucleotide sequence of pathogenic swine vesicular disease virus isolated in Japan (J1'73) and phylogenetic analysis"; *Nucleic Acids Research*; 1993; vol. 21, No. 16, pp. 3896.

Wayne M. Bares; "PCR amplification of up to 35–kb DNA with high fidelity and high yield from λbacteriophage templates"; *Proc. Natl. Acad. Sci.*; 1994; vol. 91, pp. 2216–2220.

Raul Andino et al.; "Engineering Poliovirus as a Vaccine Vector for the Expression of Diverse Antigens"; *Science*; Sep. 2, 1994; vol. 265, pp. 1448–1451.

Toru Kanno, Toru Inoue, Yifei Wang, Akinori Sarai and Shigeo Yamaguchi; "Identification of the location of antigenic sites of swine vesicular disease virus with neutralization–resistant mutants"; *Journal of General Virology*; 1995; pp. 3099–3106.

Otfried Marquardt and Volker F. Ohlinger; "Differential diagnosis and genetic analysis of the antigenically related swine vesicular disease virus and Coxsackie viruses"; *Journal of Virological Methods*; 1995; pp. 189–199.

S. Zientara, C. Sailleau, S. Moulay, A. Wade–Evans, C. Cruciere; "Application of the polymerase chain reaction to the detection of African Horse sickness viruses"; *Journal of virological Methods*; 1995; pp. 47–54.

W. Vangrysperre and K. De Clercq; "Rapid and sensitive polymerase chain reaction based detection and typing of foot–and–mouth disease virus in clinical samples and cell culture isolates, combined with a simultaneous differentiation with other genomically and/or symptomatically related viruses"; *Archives of Virology*; 1996; pp. 331–344.

Tae–Jin Yim, Shenbei Tang, and Raul Andino; "Poliovirus Recombinants Expressing Hepatitis B Virus Antigens Elicited a Humoral Immune Response in Susceptible Mice"; 1996; pp. 61–70.

Chen, B. et al., "Characterization of a Bicistronic Retroviral Vector Composed of the Swine Vesicular Disease Virus Internal Ribosome Entry Site", *Journal of Virology*, vol. 67, No. 4, pp. 2142–2148 (Apr. 1993).

* cited by examiner

Primary Examiner—Mary E. Mosher
(74) Attorney, Agent, or Firm—Merchant & Gould P.C.

(57) ABSTRACT

The present invention relates to a gene of swine vesicular disease virus (SVDV) and the mutant strains of the gene, and the expression plasmids, the preparation process thereof. The invention also relates to a vaccine for use in the prophylaxis of swine vesicular disease composition containing the mutant strains. Furthermore, the invention provides a process for differentiating mutant strains of SVDV from the wild type strain of SVDV, coxsackievirus and foot-and-mouth disease virus by polymerase chain reaction.

28 Claims, 24 Drawing Sheets

FIG. 5
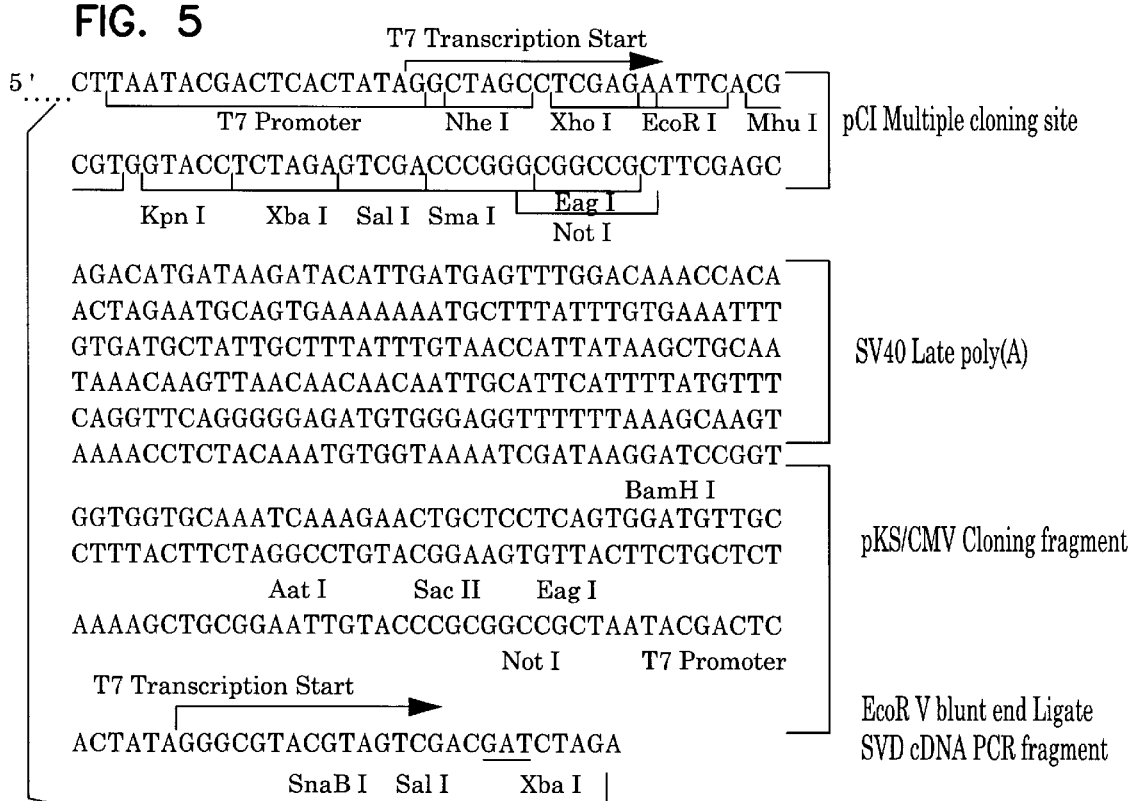
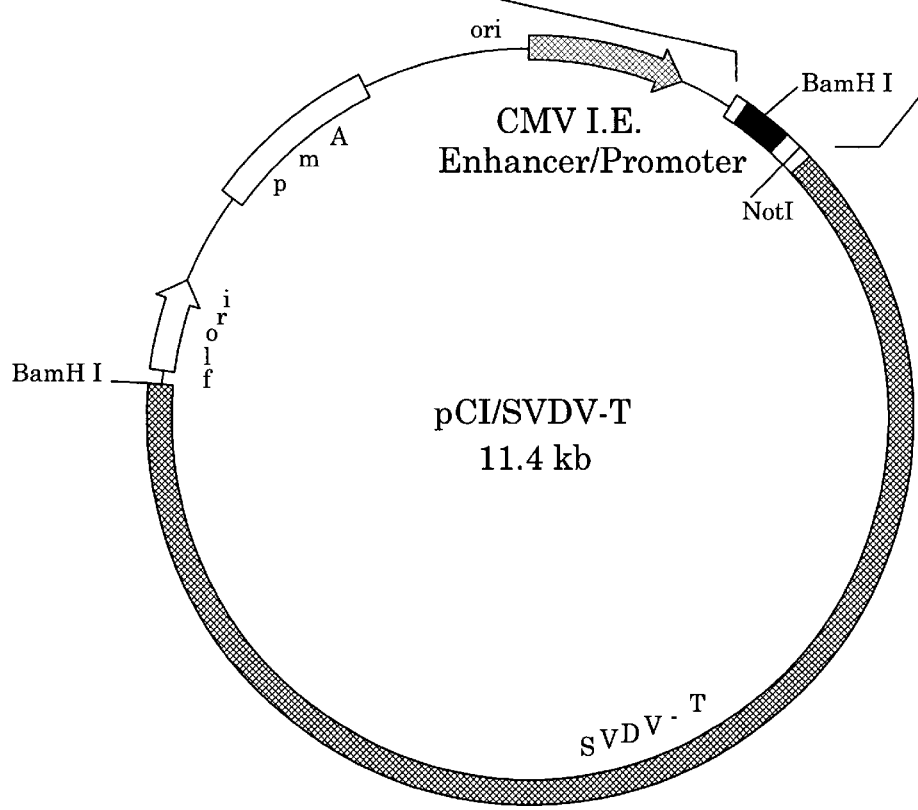

```
  1 TTAAAACAGC CTGTGGGTTG TTCCCACCCA CAGGGCCCAC TGGGCGCTAG
 51 CACACTGGTA TCACGGTACC TTTGTGCGCC TGTTTGACTT ACCCTCCCCA
101 AACGCAACTT AGAAGCACAA CTTTAAATGG TCAATAGACG GCTCAGTATG
151 CAACTGAGTC TCGATCAAGC ACTTCTGTTA CCCCGGACTG AGTACCAATA
201 GGCTGCTCAC GCGGCTGAAG GGGAAACCGT TCGTTACCCG ACTAACTACT
251 TCGAGAAACC TAGTACCACC ATGAAAGTTG CGCACGTTTC GCTCCGCACA
301 ACCCCAGTGT AGATCAGGCC GATGAGTCAC CGCAAACCCC ACGGGCGACC
351 GTGGCGGTGG CTGCGCTGGC GGCCTGCCCA TGGGCAACT CATGGGATGC
401 TTCAATACTG ACATGGTGCG AAGAGTCTAT TGAGCTAGTT GGTAGTCCTC
451 CGGCCCCTGA ATGCGGCTAA TCCTAACTGC GGAGCAGATA CCCACGCACC
501 AGTGGGCAGT CTGTCGTAAT GGGCAACTCT GCAGCGGAAC CGACTACTTT
551 GGGTGTCCGT GTTTCCTTTT ATTCTTATAC TGGCTACTTA TGGTGACAAT
601 TGAGAGATTG TAACCATATT GCTATTGGAT TGGCCACCTG GCGACGAATA
651 GAACAGTTGC TTACCTGTTT GTTAGTCTCG TATCACTGAA CTACAAAGCC
701 TTAAACACCC TTTAATTTCA TCATAACACT CAATACGTTA AAATGGGAGC
751 TCAAGTATCA ACACAAAAGA CCGGTACTCA TGAGACCAGC TTGAGTGCAG
801 CGGGCAACTC AGTCATTCAT TACACAAACA TAAACTACTA CAAGGATGCT
851 GCTTCAAATT CAGCAAATAG ACAAGACTTC ACACAGGACC CGGGGAAGTT
901 CACCGAACCT GTGAAAGACA TCATGGTCAA ATCTATGCCT GCCCTCAATT
951 CCCCATCAGC AGAGGAGTGT GGCTACAGTG ACAGGGTAAG ATCCATCACC
1001 TTAGGGAATT CAACCATAAC AACTCAAGAA TGTGCAAACG TGGTAGTTGG
1051 ATATGGGGTG TGGCCAACTT ACTTGAAGGA TGAAGAGGCA ACAGCAGAGG
1101 ATCAACCCAC TCAACCAGAT GTGGCCACGT GCAGGTTTTA CACGCTCGAA
1151 TCCGTGATGT GGCAACAGAG TTCACCAGGC TGGTGGTGGA AGTTCCCTGA
1201 CGCGTTGTCC AACATGGGGC TATTTGGGCA AAATATGCAG TACCACTACC
1251 TTGGGAGAGC CGGATACACG ATACACGTGC AGTGCAACGC GTCCAAATTT
1301 CACCAAGGGT GTCTGCTGGT GGTATGTGTG CCAGAAGCAG AGATGGGGTG
1351 TGCCACGTTG CCAATAAGC CTGACCCAAA AAGCCTGAGT AAAGGGGAAA
1401 TAGCCAACAT GTTTGAATCC CAAAGCTCCA CCGGGGAAAC GGCCGTGCAA
1451 GCTAATGTGA TCAATGCAGG CATGGGTGTT GGTGTTGGTA ATCTAACTAT
1501 CTTCCCCCAT CAGTGGATCA ACTTGCGCAC TAACAACAGC GCTACGATTG
1551 TCATGCCATA TATAAACAGC GTGCCCATGG ACAACATGTT CAGACACAAC
1601 AATTTTACAC TCATGGTCAT CCCGTTCGCC CCACTGAGTT ACAGCACAGG
1651 GGCTACCACG TACGTACCAA TCACTGTGAC AGTGGCGCCA ATGTGCGCTG
1701 AATATAATGG GCTGCGTCTA GCCGGTAAGC AAGGTTTACC AACGCTGTCG
1751 ACACCCGGGA GCAACCAGTT TCTCACGTCC GATGACTTCC AGTCACCATC
```

FIG. 7

```
1801  AGCCATGCCA CAATTCGATG TCACTCCTGA GATGGATATT CCAGGACAAG
1851  TCAACAACTT GATGGAGATT GCAGAAGTAG ATTCTGTGGT GCCTGTAAAC
1901  AACACAGAAG GGAAAGTGAT GTCAATTGAG GCGTACCAGA TACCTGTGCA
1951  ATCGAATCCA ACCAACGGTT CTCAGGTTTT TGGGTTCTCA TTGACCCCAG
2001  GGGCTAATAG TGTGTTAAAC AGGACTTTGC TGGGAGAAAT CTTAAACTAC
2051  TATGCCCATT GGTCAGGCAG CATCAAACTA ACATTTATGT TTTGCGGGTC
2101  AGCGATGGCT ACAGGAAAAT TCTTACTGGC ATACTCACCA CCGGGAGCTG
2151  GGGCACCGAC CACACGCAAG GAGGCGATGC TAGGTACTCA CGTGATCTGG
2201  GATGTGGGTC TACAATCGAG CTGCGTATTG TGTATACCAT GGATTAGTCA
2251  AACGCACTAC AGGTATGTAG TAATGGATGA ATACACCGCT GGTGGATACA
2301  TAACTTGCTG GTATCAAACA AATATTGTGG TGCCTGCAGA TGCACAGAGT
2351  GACTGTAAGA TCTTGTGTTT TGTGTCGGCA TGTAACGATT TCTCAGTTAG
2401  GATGCTCAAG GACACACCCT TTATAAAACA GGATAATTTC TTCCAAGGGC
2451  CCCCAGGAGA GGTGATGGAA AGAGCCGTTG CCCGCGTCGC TGATACTATT
2501  GGGAGCGGAC CAGTTAACTC GGAATCCATT CCAGCTCTAA CCGCCGCAGA
2551  GACAGGGCAC ACGTCACAAG TTGTACCATC AGACACAATG CAAACTAGGC
2601  ACGTGAAGAA TTATCATTCA AGGTCAGAGT CGACAGTGGA GAACTTCCTG
2651  TGCAGATCTG CATGCGTCTT CTACACCACA TACAAGAACC ATGACTCTGA
2701  TGGCGACAAC TTCGCCTACT GGGTAATCAA CACACGGCAA GTTGCTCAAC
2751  TGCGTCGGAA GCTCGAAATG TTCACGTACG CAAGATTTGA TCTGGAGTTG
2801  ACTTTCGTGA TCACTAGCAC TCAGGGACAA CCCACCGTTA AAGGTCAAGA
2851  TACACCAGTG CTCACCCACC AAATAATGTA TGTACCTCCA GGTGGCCCAG
2901  TGCCCACAAA GGTAAACAGC CACAGCTGGC AAACGTCCAC CAACCCAAGT
2951  GTGTTCTGGA CGGAAGGGAG CGCACCGCCT CGAATGTCGA TACCATTCAT
3001  TGGCATAGGC AACGCATACA GCATGTTCTA TGACGGGTGG GCCAGGTTTG
3051  ACAAGCAAGG GACATACGGC GTCAGCACAC TAAACAACAT GGGGACACTA
3101  TATATGAGAC ATGTGAATGA TGGGGGTCCC GGTCCCATTG TGAGCACAGT
3151  ACGAATTTAC TTCAAGCCAA AGCACGTCAA AACGTGGGTC CCAAGACCGC
3201  CCAGACTATG TCTATACCAA AAGGCTGGCA ACGTGAATTT TGAACCCACT
3251  GGTGTGACTG AGGGTAGGAC AGATATAACA ACCATGAAAA CCACTGGCGC
3301  CTTCGGGCAG CAGTCTGGTG CCGGTGTACGT TGGCAACTAT AGAGTGGTG
3351  ATAGACATCT CGCAACGCGC GCGGACCGGC AAAACTGTGT GTGGGAAGAC
3401  TACGACAGAG ACTTTCTAGT GAGCACCACC ACTGCACATG GCTACGACAC
3451  CATTGCCAGG TGCGATTGCA CAGCAGGAGT GTACTTCTGC GCCTCCAGAA
3501  ACAAGCACTA TCCAGTCACA TTTGAGGGGC CCGGTCTTGT GGAGGTTCAA
3551  GAGAGTGAGT ATTACCCGAA AAAGTACCAA TCCCATGTAC TGCTCGCAGC
3601  TGGATTTGCA GAGCCGGGTG ATTGTGGAGG GATTCTCAGA TGCCATCATG
3651  GGGTGATTGG CATAGTTACC GTGGGGGGAG AAGGTGTTGT TGGTTTTGCC
```

FIG. 7 (Continue)

```
3701  GATGTAAGAG ACTTGTTGTG GCTGGAGGAC GATGCCATGG AGCAAGGAGT
3751  TAGGGATTAT GTGGAACAAC TCGGCAATGC CTTCGGCTCA GGATTCACCA
3801  ATCAAATTTG CGAACAGGTT ACCCTTCTAA AAGAGTCGTT AATTGGACAG
3851  GATTCTATCC TTGAGAAGTC TCTCAAGGCC CTCGTCAAGA TAGTATCAGC
3901  ACTCGTGATC GTGGTGAGAA ATCACGATGA CCTCATTACC GTCACCGCCA
3951  CACTGGCGTT AATAGGATGT ACCACCTCAC CATGGCGCTG GCTCAAGCAG
4001  AAAGTGTCTC AGTACTATGG CATCCCCATG GCTGAAAGGC AAAATAGTGG
4051  CTGGTTAAAG AAGTTCACAG AGATGACCAA TGCCTGTAAG GGCATGGAGT
4101  GGATAGCCAT CAAGATCCAA AAGTTCATAG AGTGGTTGAA GGTTAAGATC
4151  CTGCCAGAAG TCAAGGAAAA GCATGAGTTC CTCAACAGGC TTAAACAACT
4201  ACCACTCTTG GAAAGTCAAA TAGCAACTAT TGAGCAGAGT GCACCATCTC
4251  AAAGTGACCA GGAGCAACTA TTCTCTAATG TACAGTACTT TGCCCACTAC
4301  TGTCGGAAGT ATGCACCATT GTACGCCGCT GAAGCAAAGA GAGTGTTCTC
4351  ACTTGAAAAG AAGATGAGCA ATTACATACA GTTCAAGTCC AAATGCCGTA
4401  TTGAACCTGT CTGTCTCTTG CTCCATGGCA GCCCAGGCGC TGGGAAGTCT
4451  GTGGCAACGA ACTTGATTGG GCGCTCGCTC GCTGAGAAAC TCAACAGCTC
4501  GGTGTACTCA CTACCACCAG ATCCAGACCA TTTCGATGGT TACAAACAGC
4551  AAGCTGTTGT CATCATGGAC GACTTGTGCC AGAACCCGGA CGGTAAAGAT
4601  GTGTCCTTGT TCTGTCAGAT GGTCTCCAGC GTTGACTTCG TGCCTCCCAT
4651  GGCGGCGCTT GAGGAAAAAG GCATTCTATT CACCTCGCCG TTCGTTCTCG
4701  CGTCTACCAA TGCAGGGTCA GTTAACGCCC CCACGGTCTC CGACAGTAGA
4751  GCACTCGTAA GAAGGTTCCA TTTTGACATG AACATCGAGG TTATTTCCAT
4801  GTATAGCCAG AACGGTAAGA TCAACATGCC TATGGCAGTT AAAACATGTG
4851  ATGAGGAGTG TTGCCCGGTC AACTTCAAAA AGTGCTGCCC ACTAGTGTGT
4901  GGCAAAGCTA TACAATTCAT AGACAGGAGG ACCCAAGTTA GGTATTCATT
4951  GGACATGTGG GTTACCGAAA TGTTTAGGGA GTACAATCAC AGACACAGCG
5001  TGGGGGCCAC CCTCGAGGCA TTGTTCCAAG GACCACCAGT TTATAGAGAG
5051  ATCAAAATCA GTGTTGCCCC AGAAACTCCT CCACCACCAG CAATTGCCGA
5101  CTTACTAAAA TCAGTAAACA GTGAGGCTGT GAGGGAGTAC TGCAAGGAGA
5151  AAGGGTGGCT TATACCAGAG GACGATTCCA CCCTACAGAT AGAAAAGCAT
5201  GTGAGCAGAG CGTCCATATG TTTGCAAGCT CTAACCACAT TTGTCTCGGT
5251  TGCGGGCATA ATATACATCA TCTACAAATT GTTTGCAGGT TTCCAAGGCG
5301  CATACACAGG GATGCCTAAT CAGAAGCCCA AGGTGCCCAC CCTGAGACAA
5351  GCCAAAGTGC AGGGTCCAGC GTTTGAGTTC GCCGTGGCGA TGATGAAAAG
5401  AAACACCAGT ACAGTGAAAA CTGAGTATGG TGAATTCACC ATGCTTGGGA
5451  TTTACGACAG GTGGGCGGTG TTGCCACGCC ATGCCAAACC TGGCCCCACC
5501  ATCTTGATGA ATGACCAGGT AGTCGGAGTG TTGGACGCCA AGGAACTAGT
5551  TGATAAAGAT GGGACCAACC TGGAATTGAC TCTCTTGAAG CTCAACCGCA
```

FIG. 7 (Continue)

```
5601 ACGAGAAGTT TAGAGACATC AGGGGATTCT TAGCACGAGA GGAGGTCGAA
5651 GTGAACGAAG CTGTCCTAGC AATAAACACA AGTAAATTCC CGAATATGTA
5701 CATACCCGTG GGCCGGGTAA CCGACTATGG GTTCTTAAAT CTGGGTGGAA
5751 CCCCCACGAA GAGAATGCAC ATGTACAATT TCCCAACTAG GGCAGGCCAG
5801 TGTGGGGGTG TCCTTATGTC AACAGGGAAA GTCCTGGGAA TACATGTAGG
5851 AGGGAATGGA CACCAAGGGT TTTCAGCGGC ACTCCTCAGA CACTACTTCA
5901 ATGAGGAGCA GGGTGAGATA GAATTCATTG AGAGCTCAAA GGACGCAGGA
5951 TTTCCCGTGA TCAACACTCC CAGCAAGACA AAATTGGAAC CAAGTGTGTT
6001 TCACCACGTG TTCGAGGGCA ACAAGGAACC AGCGGTTCTC AGAAATGGGG
6051 ACCCACGACT CAAGGCCAAC TTTGAGGAGG CAATCTTCTC CAAGTACATT
6101 GGCAATGTTA ACACACATGT ATACGAGTAC ATGATGGAGG CTGTAGATCA
6151 TTATGCAGGA CAACTAGCCA CACTGGACAT CAGCACGGAA CCCATGAAGC
6201 TAGAATATGC CGTGTATGGC ACTGAGGGGC TCGAAGCACT AGACCTGACC
6251 ACCAGTGCAG GTTACCCTTA TGTGGCCCTG GGTATCAAGA AAAGAGACAT
6301 CCTATCCAAG AAGACCAGAG ACCTTACCAA GCTAAAGGAA TGCATGGATA
6351 AATATGGTCT AAACTTGCCA ATGGTAACCT ATGTCAAGGA TGAGTTGAGA
6401 TCTGCCGACA AAGTGGCCAA GGGAAAATCC AGGCTCATCG AGGCTTCTAG
6451 CCTCAACGAC TCAGTAGCAA TGAGGCAGAC ATTTGGAAAC CTATATAAGA
6501 CTTTCCACCT CAACCCGGGC ATCCGTTACG GTAGCGCCGT TGGGTGTGA
6551 CCAAATGTCT TTTGGAGCAA GATCCCCGTT ATGCTCGATG GACATCTCAT
6601 AGCGTTTGAC TATTCAGGCT ATGACGCCAG CCTCAGCCCA GTGTGGTTTA
6651 CGTGCTTGAA ACTCCTCCTG GAGAAGCTAG GGTACACAAA CAAGGAAACG
6701 AACTACATAG ACTACCTCTG TAATTCCCAC CACCTGTACA GGGACAAACA
6751 CTACTTTGTG AGGGGCGGCA TGCCATCAGG ATGCTCAGGC ACTAGCATAT
6801 TTAATTCCAT GATTAACAAC ATCATAATCA GAACCCTCAT GCTGAAGGTT
6851 TATAAAGGCA TTGATTTGGA CCAATTCAGA ATGATTGCAT ATGGGGATGA
6901 TGTGATAGCT TCATACCCGT GGCCTATCGA TGCCTCACTG CTAGCTGAAG
6951 CAGGGAAGGG TTATGGCTTG ATCATGACCC CAGCAGATAA AGGCGAGTGT
7001 TTCAGTGAGG TAACCTGGAC AAACGTGACC TTCCTGAAAA GGTACTTCAG
7051 GGCAGATGAA CAGTACCCAT TTTTGGTCCA TCCTGTCATG CCAATGAAGG
7101 ATATACACGA ATCCATTAGG TGGACTAAAG ATCCTAAGAA CACACAGGAT
7151 CACGTGCGCT CGCTGTGTTT ATTGGCTTGG CACAACGGGG AGCACGAATA
7201 TGAGGAGTTT ATTCGTAAGA TCAGAAGCGT GCCCGTAGGG CGCTGCTTGT
7251 CCCTCCCTGC GTTTTCAACG CTGCGCAGGA AGTGGTTGGA CTCCTTTTAA
7301 AATTAGAGCA CAATTAGTCA ATCATAATTG GCTCAACCCT ACCGCATGAA
7351 CCGAACTTGA TAAAAGTGCG GTAAAGGTAA ATTCTCCGTA TTCGGTGCGG
```

```
                                    T7 Transcription Start
   5'.....CTTAATACGACTCACTATAGGCGTACGTAGTCGACGATCTAGA
              T7 Promoter            SnaB I    Sal I
                                 T7
                                 SnaB I
                                 Sal I
                                    (do not cut)
``` pCI(ΔEag I)/ SVD V-T
11 kb

- Amp
- ori
- CMV I.E. Enhancer/Promoter
- intron
- SVDV-T
- BamH I

```
                                                    T7 Transcription Start
         5'.....CTTAATACGACTCACTATAGGCGTACGTAGTCGACGATCTAGA
                    T7 Promoter          SnaB I  Sal I
```

Plasmid map: pCI(ΔEag I)/ SVD V-T(ΔSph I), 11kb

Features: Amp, ori, CMV I.E. Enhancer/Promoter, Hind III, T7/SnaB I/Sal I, SVDV-T, Sph I, BamH I, intron FIG. 12
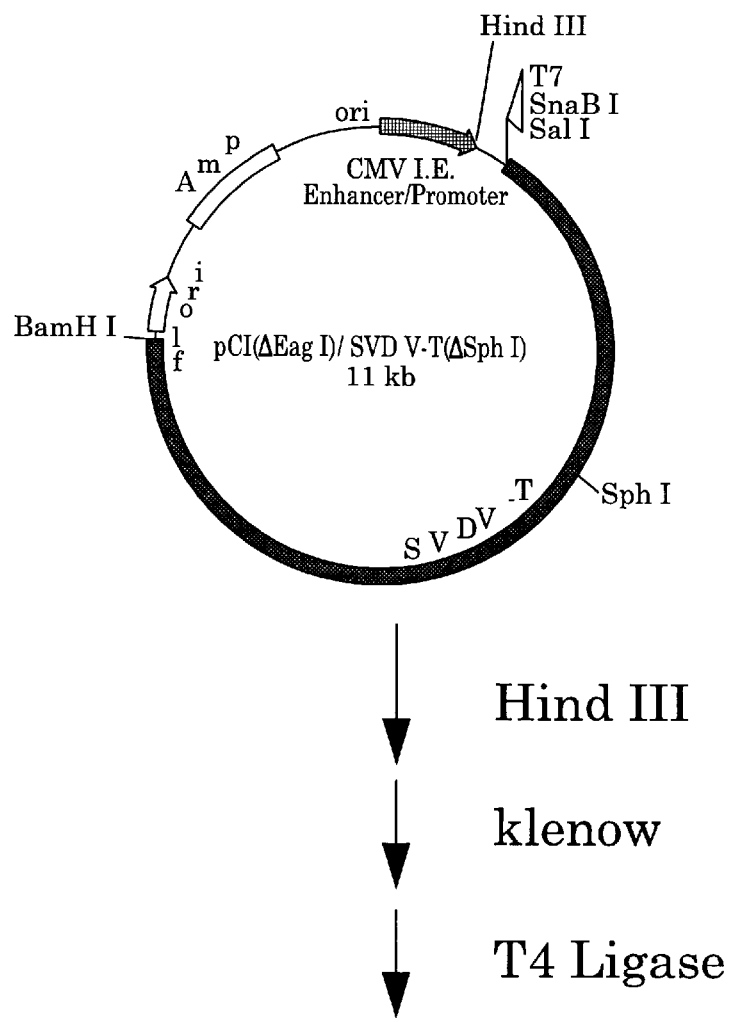
Hind III
klenow
T4 Ligase
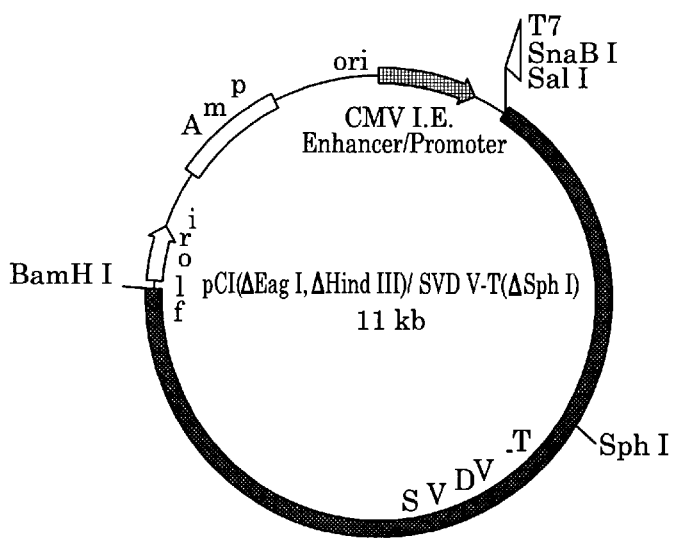

FIG. 14

SWINE VESICULAR DISEASE VIRUS AND MUTANT STRAINS AND PREPARATION PROCESS AND USE THEREOF

FIELD OF THE PRESENT INVENTION

The present invention relates to a gene of swine vesicular disease virus (SVDV) and the mutant strains of the gene, and the expression plasmids, the preparation process and the use thereof. The present invention also relates to a vaccine composition containing the strains.

BACKGROUND OF THE PRESENT INVENTION

Swine vesicular disease is a viral disease by contact infection and its vesicular pathology is essentially similar to foot-and-mouth disease in anatomy and histology. In addition to vesicular pathology, any pathology during autopsy cannot be found in other tissues. The vesicles generally occur in crown belt, the area between toe and hoof, nose, mucous-membrane of oral cavity and tongue. Swine vesicular disease is similar to foot-and-mouth disease in clinical conditions. Although a swine contracting swine vesicular disease will not die, the infected swine will have the conditions including pain, creep and delayed growth and development. Since swine vesicular disease is very similar to foot-and-mouth disease in clinical conditions, it is easily to cause a mistaken examination to affect the prevention of foot-and-mouth disease, which is a highly acute and infectious disease of livestock and wild cloven-hoofed animals and deeply strike the livestock industry; therefore, the countries having progress in livestock industry regard foot-and-mouth disease as the first preventive object. To effectively control foot-and-mouth disease, the developed countries regard swine vesicular disease as malignant infectious disease and adopt cleaning policy, i.e., the extermination of the swines contracting swine vesicular disease. Further, these countries strictly control imported pork and prevent the swines contracting swine vesicular disease into the countries.

The causative agent of swine vesicular disease is swine vesicular disease virus (SVDV). SVDV belongs to the genus enterovirus of the Picornaviridae. The genome of SVDV is a single-stranded RNA with a positive polarity, 7400 nucleotides long and consists of P-1, P-2 and P-3 regions. All viral genes only have one open reading frame and can synthesize a large polyprotein. The polyprotein can be cleaved by virus-specific proteinase to form a mature viral protein. The polyprotein of P-1 region includes four capsid proteins, i.e., VP1, VP2, VP3 and VP4 (Toru Inoue et al, J. gen. Virology (1989), 70, 919–934). The epitope of SVDV is mainly on amino acid residues 87, 88, 272 and 275 of VP1; 70, 154, 163 and 233 of VP2; 60, 73 and 76 of VP3 (Toru Kanno et al, J. gen. Virology (1995), 76, 3099–3106). The polyprotein of P-2 region includes 3 proteins: 2A, 2B and 2C wherein 2A is a protein cleaving enzyme. The polyprotein of P-3 region includes 4 proteins: 3A, 3B, 3C and 3D; wherein 3A is a protein-cleaving enzyme and 3D is an RNA polymerase.

As previously reported, the genes of SVDV only have 7400 base pairs and encode 11 proteins. Each protein is essential for viral survival. Up to now, none of the prior art discloses that the deletion of any fragments of viral protein will not affect the viral survival.

The known papers have disclosed all cDNA sequences of SVDV strains H/3' 76 (Toru Inoue et al, J. gen. Virology (1989), 70, 919–934), J 1' 73 (Toru Inoue et al, Nucleic Acids Research, 1993, Vol. 21. No.16, 3896) and UKG/27/72 (P. Seechurn et al. Virus Research 16, 255–274 (1990)). The homology among the strains is larger than 98%.

Furthermore, the homology between coxsackievirus B5 and the capsid protein of swine vesicular virus is 92–96% but between coxsackievirus 2A and the capsid protein of swine vesicular virus is 86.7–88%. Although the clinical conditions of foot-and-mouth disease are very similar to those of swine vesicular disease, the genetic homology between foot-and-mouth disease virus (FMDV) and SVDV is lowered to approximately 25%. The conventional diagnosis and identification of FMDV and SVDV are depended on serological assay. However, since the technique of DNA polymerase chain reaction is greatly advanced in detecting DNA sequence in a sample and is easier and quicker than serological assay, the samples having similar sequences can be differentiated according to appropriate primer design. Therefore, it has been reported that the use of polymerase chain reaction to diagnosis and identify the viruses having similar clinical conditions or capsid proteins (Otfried Marquardt et al. J. Virological Methods 53(1995) 189–199, S. Zientara et al. J. Virological Methods 53(1995) 47–54 and Arch Virol (1996) 141:331–344). Due to the progress of PCR technique, especially directed to the improvement of the quantitative PCR technique, the methods by PCR technique for examining swine vesicular disease, coxsackie disease and foot-and-mouth disease will be more and more widespread.

In 1981, Baltimore cloned cDNA of full-length poliovirus, which belongs to Picornaviridae, to expression vector of mammalian cells containing SV40 promoter, and then transfected HeLa cells with the vector to produce infectious poliovirus (Baltimore et. al. Science 214, 916–919 (1981)). Thus, any person skilled in the art can modify cDNA sequence of RNA virus in expression plasmids and then transfected suitable host cells with the plasmids to produce mutagenic RNA virus. Therefore, the genetic recombination of DNA virus can be easily and rapidly operated in DNA level. Thereafter, the strains mutated on epitopes of poliovirus have been made and the vectors for use in polyvalent vaccine have been developed (Paul Andino et al. Science 265 (1994) 1448–1451; Tae-Jin Yim et al. Virology 218, 61–70 (1996)).

In 1990, Toru Inoue cloned cDNA of SVDV(Japan H/3' 76 strain), which belongs to Picornaviridae, to expression plasmid pSVL of mammalian cells containing SV40 promoter, and then transfected IBRS-2 cells with the plasmid to produce SVDV(Toru Inoue et al J. gen. Virology (1990), 71, 1835–1838). However, the viral plaques formed by the recovered virus are smatter than those of parental virus (H/3' 76 strain). It may be resulted from mutagenesis during the cloning in complex expression plasmids (through about 10 times cloning steps).

In current livestock industry, there is no vaccine having good immunity for swine vesicular disease and differentiating from wild type strain of SVDV to prevent swine vesicular disease. Therefore, it urgently requires a vaccine having mutant strains capable of differentiating from wild type strain of SVDV to immunize swines to decrease economic loss.

SUMMARY OF THE PRESENT INVENTION

It is an object of the present invention to provide a full-length cDNA sequence of Taiwan Yu-Li strain of SVDV.

It is also an object of the present invention to provide the gene of mutant strain of SVDV, and the mutant strains of SVDV and the expression plasmids thereof.

It is an other object of the present invention to provide a process for preparing the mutant strains of SVDV.

It is a further object of the present invention to provide a vaccine composition for use in prophylaxis of swine vesicular disease.

It is a further object of the present invention to provide a method for use in the prophylaxis and extermination of the swine vesicular disease.

It is a still further object of the present invention to provide a process for differentiating from coxsackievirus and FMDV.

BRIEF DESCRIPTION OF THE DRAWINGS

FIG. 2 is a diagram illustrating a construction of the expression plasmid pKS/CMV-SVDV-T.

FIG. 4 is a diagram illustrating a construction of the expression plasmid pCI/SVDV-T.

FIG. 5 is a diagram illustrating a restriction map of the expression plasmid pCI/SVDV-T (including SEQ ID NO: 26–31).

FIG. 7 is a diagram illustrating a full-length cDNA nucleotide sequence of Taiwan Yu-Li strain of SVDV (SEQ ID NO: 1).

FIG. 8 is a diagram illustrating a construction of the plasmid pCI(Δ Eag I)/SVDV-T.

FIG. 9 is a diagram illustrating a restriction map of the plasmid pCI(Δ Eag I)/SVDV-T (including SEQ ID NO:32).

Figure 10:
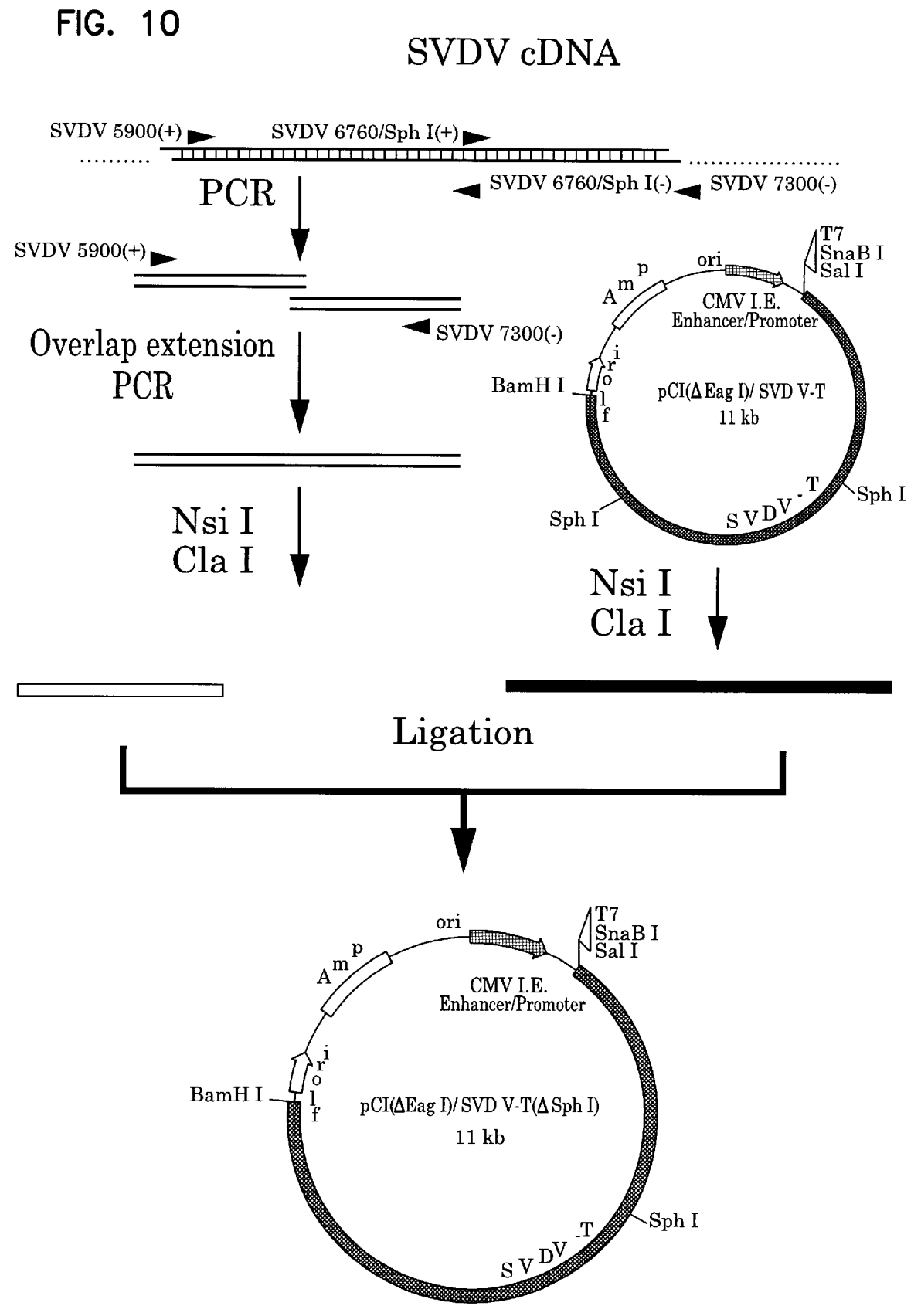

FIG. 10 is a diagram illustrating a construction of the plasmid pCI(Δ Eag I)/SVDV-T(Δ Sph I).

FIG. 11 is a diagram illustrating a restriction map of the plasmid pCI(Δ Eag I)/SVDV-T(Δ Sph I) (including SEQ ID NO:32).

FIG. 12 is a diagram illustrating a construction of the plasmid pCI(ΔEag I, Δ Hind III)/SVDV-T(Δ Sph I).

FIG. 14 is a diagram illustrating a construction of the plasmid pCI(Δ Eag I, Δ Hind III)/SVDV-T(Δ Sph I)/H21.

DETAILED DESCRIPTION OF THE PRESENT INVENTION

Figure 1:
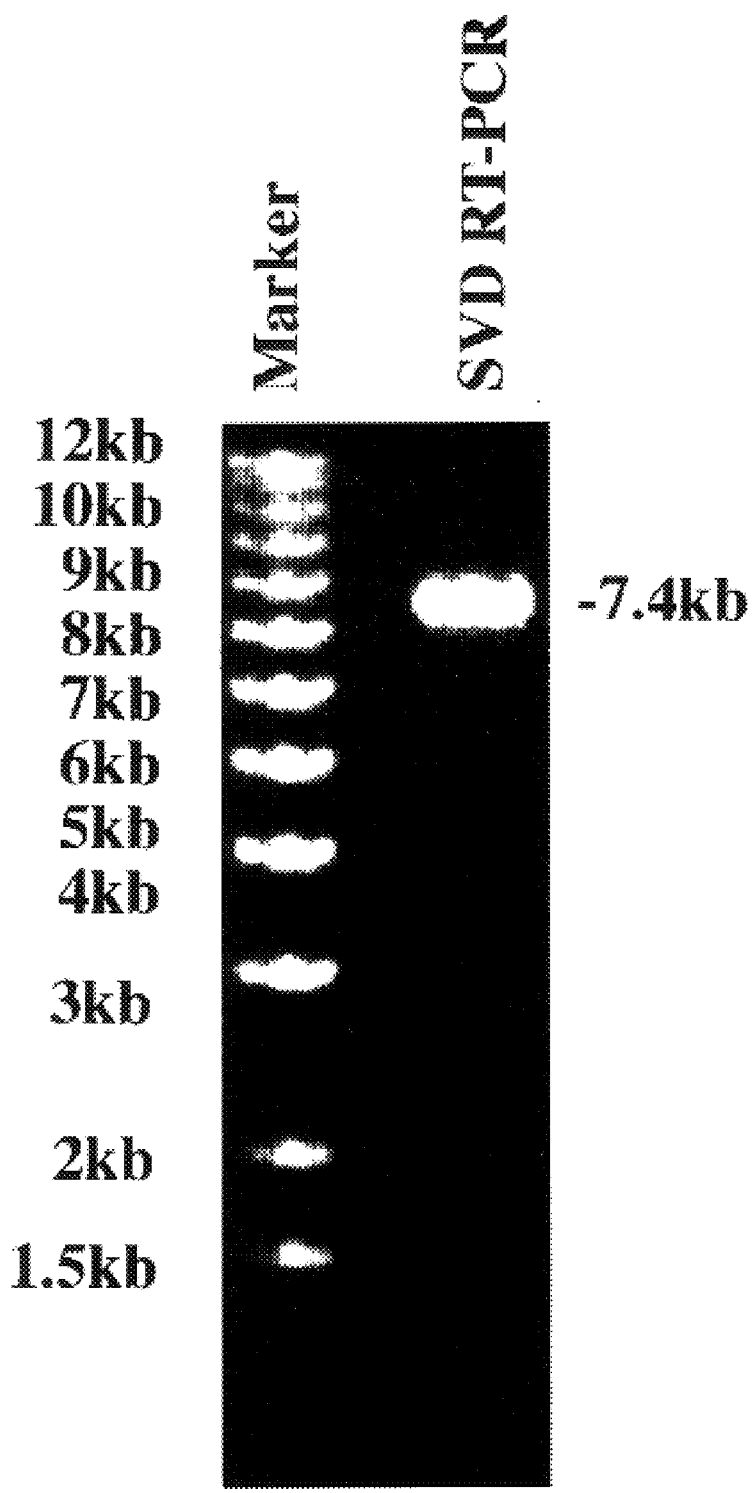
FIG. 1 is a diagram illustrating a full-length cDNA sequence of SVDV prepared by reverse transcriptase—polymerase chain reaction (RT-PCR).

The present invention firstly provides a full-length cDNA sequence of Taiwan Yu-Li strain of swine vesicular disease virus (SVDV) and the degenerative sequences thereof, which is prepared by the use of RNA of Taiwan Yu-Li strain of SVDV as a template according to reverse transcriptase polymerase chain reaction. The cDNA sequence is cloned to expression vectors containing a promoter (such as CMV promoter) and then host cells are transfected with the vectors to produce INFECTIOUS SVDV.

All genes of SVDV encode 11 proteins. Each protein is essential for viral survival. Up to now, none of the prior art reports that the deletion of any fragments of viral protein will not affect the viral survival. The present invention further provides a gene of mutant strains of SVDV differentiating from that of the wild type strain of SVDV. When constructing the mutant strains of SVDV for use in vaccine, there is no way to delete antigenic fragments of the viral protein adopted by the conventional method to achieve the differentiation. Therefore, an alternative method should be made to achieve the purpose of the invention. For example, when constructing the mutant strains of pseudorabies vaccine capable of determining pseudorabies virus, it can be made by deleting gp1 gene of the virus so that the virus no longer produces gp1 protein and still can survive to achieve the purpose of differentiating from the wild type strain. Under the circumstances without affecting viral survival, the present invention uses the replacement of epitope gene of capsid protein to achieve the purpose of differentiating from the wild type strain. Accordingly, the present invention also provides a gene of mutant strain H21 of SVDV, which comprises the sequences as Taiwan Yu-Li strain of SVDV wherein base pairs positioned on 2705–2710 are replaced by GAAAGC, [SEQ ID NO:3] and the functional fragments and the degenerative sequences thereof.

The present invention further provides a gene of mutant strain N3 of SVDV, which comprises the sequences as Taiwan Yu-Li strain of SVDV wherein base pairs positioned on 2693–2710 are replaced by GACAACGGCGCTGAAAGC, [SEQ ID NO:4] and the functional fragments and the degenerative sequences thereof.

The present invention still further provides a gene of mutant strain SP7 of SVDV, which comprises the sequences as Taiwan Yu-Li strain of SVDV wherein base pairs positioned on 2705–2710 are replaced by GGCTCCACCACAAACAAGGATAAGAGC, [SEQ ID NO:5] and the functional fragments and the degenerative sequences thereof.

To avoid causing mutation during many times of cloning steps, the present invention has disclosed a process comprising reverse-transcripting RNA of Taiwan Yu-Li strain of SVDV as a template to a single strand DNA, preparing 7.4 kb fill-length cDNA by extra-length PCR technique (Wayne M. Barnes, Proc. Natl. Acad. Sci. USA Vol. 91, pp 2216–2220, March 1994) and cloning cDNA into a expression vector containing a promoter (such as CMV promoter) to form a INFECTIOUS expression vector. The appropriate host cells are transfected with the expression vector to produce a INFECTIOUS virus. SVDV prepared by the process of the present invention has the same with the parental virus in potency, viral plaque size and serum neutralization against SVDV.

The mutant strains of SVDV can be prepared by the modification of cDNA sequence of SVDV in the expression plasmids. The mutant strains have a better efficacy in the induction of the neutralization antibody produced by the mice than wild type strains. Due to the m differentiation from the wild type strains, the mutant strains can be used in the policy of exterminating the swine contracting swine vesicular disease.

Accordingly, the present invention also provides the following mutant strains:

A mutant strain N3 of SVDV, which comprises the gene sequences denoted as Taiwan Yu-Li strain of SVDV wherein base pairs positioned on 2693–2710 are replaced by GACAACGGCGCTGAAAGC, [SEQ ID NO: 4] and the functional fragments and the degenerative sequences thereof.

A mutant strain H21 of SVDV, which comprises the gene sequences denoted as Taiwan Yu-Li strain of SVDV wherein base pairs positioned on 2705–2710 are replaced by GAAAGC, [SEQ ID NO: 3] and the functional fragments and the degenerative sequences thereof.

A mutant strain SP7 of SVDV, which comprises the gene sequences as Taiwan Yu-Li strain of SVDV wherein base pairs positioned on 2705–2710 are replaced by GGCTCCACCACAAACAAGGATAAGAGC, [SEQ ID NO: 5] and the functional fragments and the degenerative sequences thereof.

The present invention also provides an expression plasmid comprising full-length cDNA of SVDV and the mutant strain thereof.

The present invention further provides an expression plasmid comprising the sequences of Taiwan Yu-Li strain of SVDV.

The present invention still further provides an expression plasmid comprising the sequences mutagenized on the regions 1, 2 or 3 of the capsid protein of SVDV.

In particular, the present invention provides an expression plasmid comprising the sequences mutagenized on the amino acid positions 84–88 of SVDV.

The present invention further provides the expression plasmids of SVDV, which are selected from pCI/SVDV-T (which has been deposited on Aug. 4, 1998 with the China Center for Type Culture Collection (CCTCC), Wuhan University, Wuhan 430072 Republic of China under Accession No. M 98013), pCI (Δ Eag I, Δ HindIII)/SVDV-T (Δ Sph I)/H21 (which has been deposited on Aug. 4, 1998, with the CCTCC under Accession No. M 98011), pCI (Δ Eag I, Δ Hind III)/SVDV-T(Δ Sph I)/SP7 (which has been deposited on Aug. 4, 1998, with the CCTCC under Accession No. M 98012), or pCI/(Δ Eag I, Δ Hind III)/SVDV-T(Δ Sph I)/N3 (which has been deposited on Aug. 4, 1998 with the CCTCC under Accession No. M 98010).

The present invention further provides a process of preparing the mutant strain of SVDV, comprising the following steps:

(1) constructing an expression plasmid containing full-length cDNA of SVDV, (2) modifying the full-length cDNA of SVDV in the expression plasmid to construct an expression plasmid containing the sequences of the mutant strain of SVDV, and (3) transfecting the appropriate host cells with the expression plasmid containing the sequences of the mutant strain of SVDV to produce the mutant strain of SVDV.

The expression plasmids of SVDV disclosed in the present invention are not only for use in the recombination of SVDV cDNA to produce the mutant strains of SVDV, but link heterologous genes to form a vector expressed heterologous genes such as a vector of polyvalent vaccine. In addition, the vaccine of the present invention can differentiate from the swine vesicular disease caused by wild type strains of SVDV. Therefore, the vaccine for use in prophylaxis of the swine vesicular disease is not only for use in the prophylaxis of the swine vesicular disease, but the prophylaxis of mouth-and-foot disease. When conducting cleaning policy, the vaccine comprising the mutant strains of SVDV can differentiate from the wild type strains of SVDV to reduce economic loss.

Accordingly, the present invention provides a vaccine composition for use in prophylaxis of swine vesicular disease, comprising the mutant strains of SVDV of the present invention and an adjuvant for the vaccine. The vaccine composition is prepared by propagating the host cells transfected With the mutant strains of the present invention and adding appropriate adjuvant.

The present invention also discloses a process for differentiating mutant strains of SVDV from the wild type strain of SVDV by polymerase chain reaction. The 5' and 3' ends of primer pairs are respectively designed to VP1 and 2A proteinase regions, which correspond to base pairs 2692–2709 and 3358–3375 of the full-length cDNA of SVDV. Therefore, the process can be used in the differentiation of the strains of SVDV from coxsackievirus and FMDV.

Accordingly, the present invention provides a process for differentiating mutant strains N3, H21 and SP7 from the wild type strain of SVDV by polymerase chain reaction, characterized in that DNA primers used in the polymerase chain reaction are respectively located on base pairs 2692–2709 and 3358–3375 of the cDNA of SVDV.

The present invention further provides a process for differentiating from coxsackievirus and foot-and-mouth disease virus by polymerase chain reaction, characterized in that DNA primers used in the polymerase chain reaction are respectively located on base pairs 2692–2709 and 3358–3375 of the cDNA of SVDV.

Since the vaccine of the present invention can differentiate from the wild type strains of SVDV by polymerase chain reaction or enzymatic immunization reaction, the present invention is not only for the prophylaxis of swine vesicular disease, but for the eradication of swine contracting wild type strain of SVDV to achieve the purpose of eradicating SVDV.

Accordingly, the present invention provides a method for preventing and eradicating the swine vesicular disease, comprising the following steps:

(1) immunizing a swine with a vaccine containing the mutant strains of SVDV;

(2) detecting a swine contracting wild type strain of SVDV with polymerase chain reaction or enzymatic immunization reaction; and (3) eradicating the swine contracting wild type strain of SVDV.

In particular, the present invention provides a method for use in the prophylaxis and eradication of the swine vesicular disease, wherein the mutant strains of SVDV in the step (1) are selected from the group consisting of mutant strains N3, H21 and SP7 of SVDV, and the primer pairs used in the polymerase chain reaction in the step (2) are located on base pairs 2692–2709 and 3358–3375 of the cDNA of SVDV.

The term "appropriate host cells" used herein relates to the conventional host cells for use in genetic recombinant technique, which includes E. Coli, yeast, insect cells etc., or known cell strains for use in the culture technique of PR virus such as pig kidney cells-MVPK, PK-2 and PK-15; swine testicle cells (ST); calf embryo spleen cells; Madin-Darby calf spleen cells; monkey spleen cells-vero; rabbit spleen cells-RK13; baby hamster kidney (BHK); mouse fibroblast-LM (TK-).

The term "appropriate vector" used herein relates to the conventional vectors for use in genetic recombinant technique. For instance, a vector comprising the promoter such as T5, T7, SP6, Ptac, lac, trp for use in E. Coli; a vector for use in yeast; vectors for use in insect cells; or a virus for use in cells.

The following examples further illustrate the present invention, but are not intended to limit the scope of the present invention. The modifications and substitutions known to those skilled in the art are still within the scope and spirit of the present invention,

EXAMPLES

Example 1
Cultivation and purification of SVDV

Taiwan Yu-Li strain of SVDV and MVPK cells were provided by Dr. S. S. Lai, Department of Veterinary, National Taiwan University.

MVPK cells were used for culturing SVDV. The culture broth used was MEM supplemented with 5% fetal calf serum. MVPK cells were cultured in the incubator under 5% $CO_2$ at 37° C. When monolayer cells were formed, the culture broth was removed and about 0.1 MOI of Taiwan Yu-Li strain of SVDV was inoculated into each of the T-175 culture flasks. Then, the flasks were incubated in the incubator at 37° C. with mild shaking for 1 hour and then transferred into the incubator containing 5% $CO_2$ at 37° C. to allow cell growth. When the cytopathic effect (CPE) reached 90%, the broth was collected and centrifuged at 4° C. for 10 minutes (3000 rpm/min). The pellet was disregarded and the viral cytolyzing solution was harvested. The titer of the viral cytolyzing solution was 109 pfu/ml. PEG 6000 was then added until the concentration reached 8%. The mixture was stirred at 4° C. for 6 hours and then centrifuged for 30 minutes (6000 rpm/min). The pellet was resuspended in 1/100 original volume of 1×TEN buffer (0.01 m Tris-HCl, pH 7.5, 0.1 M NaCl, 1 mM EDTA). The virus was then purified by CsCl gradient centrifugation (the gradients from bottom to top were 2 ml×1.45 g/ml, 2 ml×1.39 g/ml, 2 ml×1.35 g/ml, and 2 ml×1.25 g/ml). 2 ml of the viral cytolyzing solution was placed on the top of the gradient centrifugation column and then subjected to centrifugation at 4° C. for 4 hours (3600 rpm/min). Virus particles within the layer with a density of 1.34 g/ml were collected and the CsCl-containing virus particle solution was dialyzed with 1×TEN buffer. The titer of the purified SVDV was determined in the MVPK cell assay as $10^{11}$ pfu/ml.

Example 2
Preparation of the full-length cDNA of SVDV
(1) Purification of virus RNA 0.75 ml of TRIzol LS reagent (BRL) was added into 0.25 ml of the virus solution. The mixture was gently shaken for 30 seconds and then left for 5 minutes. Then, 0.2 ml of chloroform was added. The mixture was vigorously shaken for 30 seconds, set aside for 5 minutes and then centrifuged at 4° C. for 15 minutes (12000 rpm/min). The supernatant was collected and into which was added 0.5 ml of isopropanol. The mixture was left at room temperature for 10 minutes and then centrifuged at 4° C. for 10 minutes (12000 rpm/min). The supernatant was disregarded and the pellet was washed with 1 ml of 75% ethanol. The RNA was dissolved in water and RNA concentration was determined with UV at 260 nm. The size of the purified RNA was determined with 1% agarose gel as 7.4 kb.

(2) Synthesis of first strand cDNA

One $\mu$l of oligo dT (33 mer) was added into 10 pi (5 $\mu$g,) of the RNA. The mixture was heated to 95° C. for 2 minutes and then placed on ice for 10 minutes. One pi of RNasin (200 unit/$\mu$l, Gibco-BRL), 1 $\mu$l of reverse transcriptase (200 unit/$\mu$l, Super Script TM Gibco BRL), 4 $\mu$l of 5×RT buffer, 0.4 $\mu$l of 25 mM dNTPs and 2 $\mu$l of 0.1 M DTT were added and well mixed. The reaction mixture was incubated at 25° C. for 10 minutes, followed by 42° C. for 1 hour, and finally at 90° C. for 10 minutes. After the reaction mixture was cooled on ice, 1 $\mu$l of RNaseH (2 unit/$\mu$l, Gibco BRL) was added and the reaction was incubated at 37° C. for 20 minutes. The product was purified using QIA Quick Spin Plasmid kit (QIAGEN) and the first strand cDNA was eluted with 50 pi of water.

(3) Synthesis of cDNA by polymerase chain reaction

Into 5 $\mu$l of the first strand cDNA were added 4 $\mu$l of 2.5 mM dNTPs, 5 $\mu$l of 10×ExTaq reaction solution (TaKaRa), 0.5 $\mu$l of the 5' primer (0.2 $\mu$g/$\mu$l) having the sequence GCTCTAGATTAAAACAGCCTGTGGGTTGTTCC, [SEQ ID NO: 6] 0.5 $\mu$l of the 3' primer (0.2 $\mu$g/$\mu$l) having the sequence CGGGATCC(T)$_{32}$, [SEQ ID NO: 7] 35$\mu$l of water d 0.25 $\mu$l of ExTag (5 units/$\mu$l, TaKaRa). 50 $\mu$l of mineral oil was added to the top of the reaction mixture. The reaction conditions of the thermal cycler (RoboCycle, Stratagene) were set as follows: 1 cycle of 94° C. for 1 minute, followed by 30 cycles consisting of 94° C. for 30 seconds, 60° C. for 1 minute and 72° C. for 7.5 minutes, and followed by 1 cycle of 72° C. for 10 minutes. The PCR product was purified using QIA Quick Spin PCR purification kit (QIAGEN) and eluted with 100 $\mu$l of water. The PCR product was analyzed with 0.8% agarose gel electrophoresis. As shown in FIG. 1, the results confirmed that the full-length cDNA of SVDV with a total length of about 7.4 kb was prepared.

Figure 2:
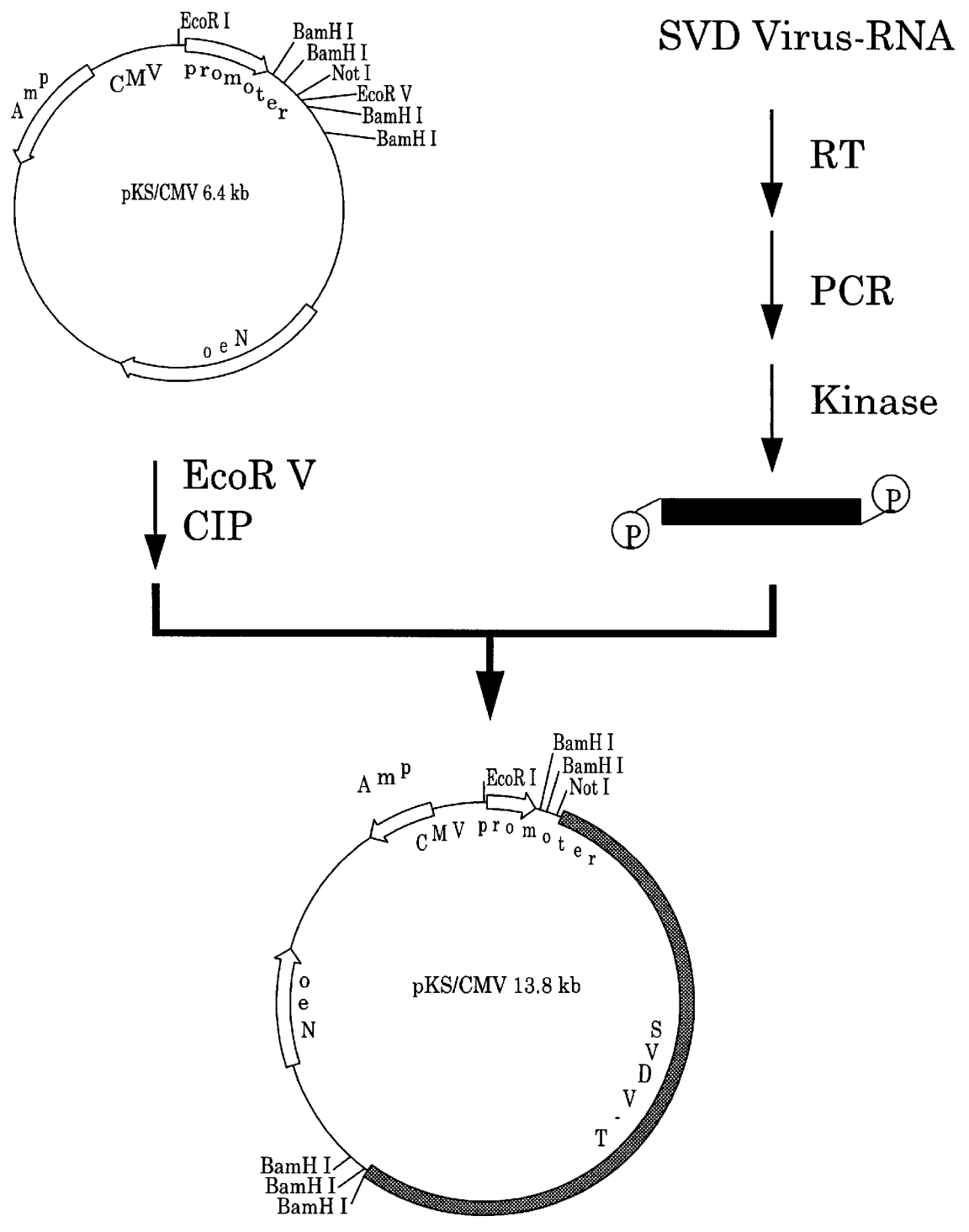

Example 3
Construction of the expression plasmid of SVDV
(1) Construction of expression plasmid pKS/CMV-SVDV-T Expression plasmid pKS/CMV-SVDV-T was constructed as illustrated in FIG. 2.

Figure 3:
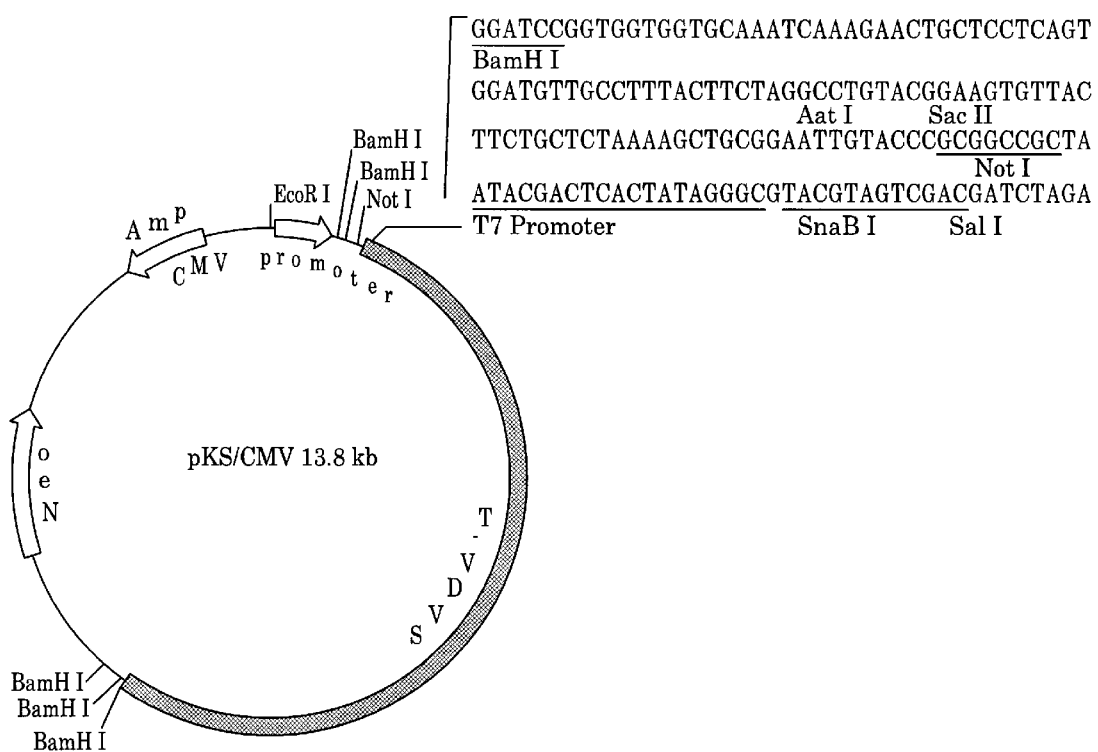
FIG. 3 is a diagram illustrating a restriction map of the expression plasmid pKS/CMV-SVDV-T (including SEQ ID NO:25).

The EcoRV site in the pKS/CMV vector was digested with EcoRV restriction endonuclease. The 5' phosphoryl residue was removed by basic dephosphorylase (CIP, New England Biolabs). After purification, the treated vector was stored at 4° C. The 7.4 kb cDNA of SVDV was phosphorylated by T4 polynucleotide kinase (New England Biolabs). After purification, the treated cDNA was ligated to the treated vector with T4 DNA ligase for 16 hours at 16° C. The ligation mixture was then used to transform E. Coli DH5α strain. After screening, a plasmid larger than the pKS/CMV E. Coli vector was obtained. With the subsequent restriction endonuclease analysis and the DNA sequencing with Sanger's method using Sequence version 2.0 DNA sequencing kit (United States Biochemical) and T7 promoter sequence (ATTAATACGACTCACTATAGG) [SEQ ID NO: 8] as primer, the cloned 7.4 kb fragment was confirmed to be the full-length cDNA of SVDV. The restriction map of the plasmid is shown in FIG. 3.

(2) Construction of expression plasmid pCI/SVDV-T

Figure 4:
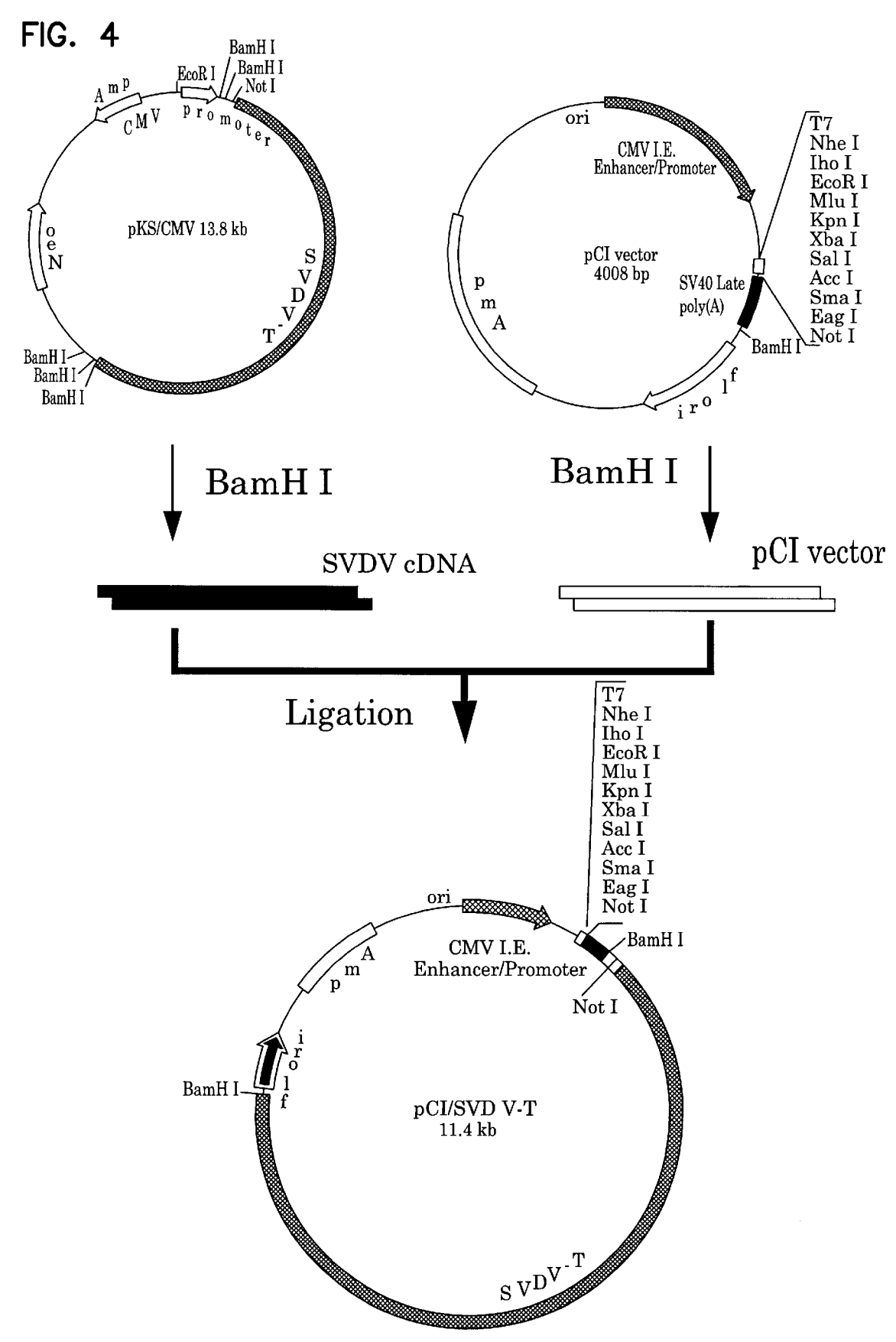

Expression plasmid pCI/SVDV-T was constructed as illustrated in FIG. 4.

The full-length cDNA of SVDV was digested from the expression plasmid pKS/CMV-SVDV-T with BamHI restriction endonuclease. DNA were separated with 0.8% agarose gel electrophoresis. About 7.4 kb of the cDNA fragment was cut. After purification, the cDNA was stored at 4° C. The pCI vector (Promega) was also digested with BamHI restriction endonuclease. The phosphoryl residues at both ends were then removed by basic dephosphorylase to prevent the vector from auto-ligation. After purification, the treated vector was ligated to the 7.4 kb DNA fragment with T4 DNA ligase for 16 hours at 16° C. The ligation mixture was then used to transform E. Coli DH5α strain. After screening, a plasmid larger than pCI was obtained. With the subsequent restriction endonuclease analysis and DNA sequencing, it was confirmed that the cDNA of SVDV was ligated to the pCI vector to construct pCI/SVDV-T expression plasmid. The restriction map of the plasmid is shown in FIG. 5.

Figure 6A:
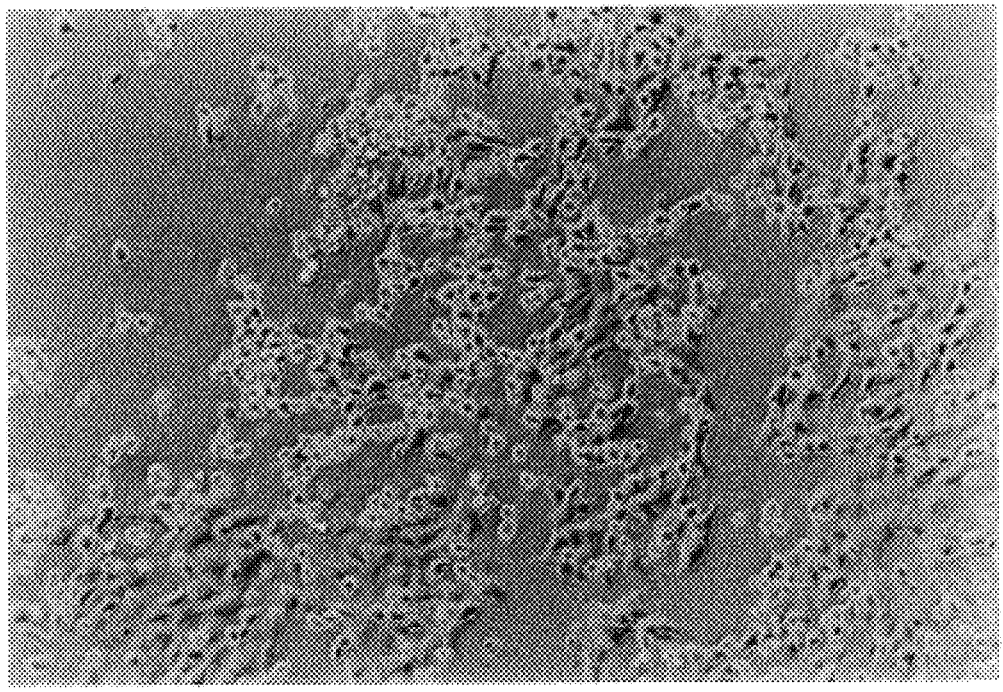
FIG. 6 is a photograph illustrating viral plaques of SVDV appeared on MPVK cells after (a) 24 hours and (b) 48 hours of the cells being transfected with pCI/SVDV-T.
Figure 6B:
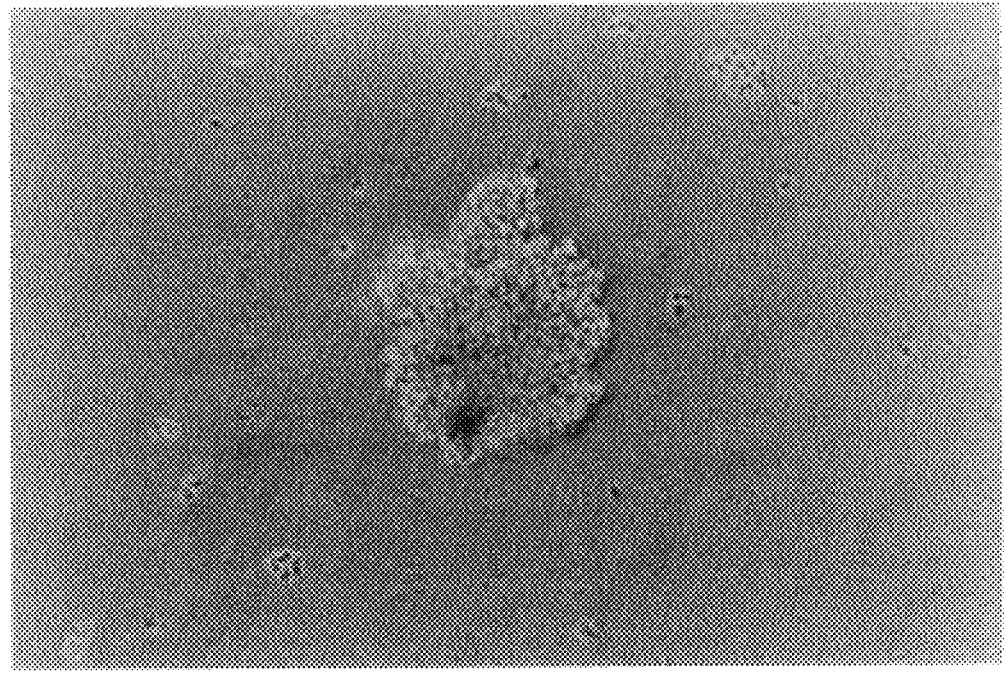

Example 4
Preparation of SVDV with the expression plasmid of SVDV
$1-2 \times 10^5$ MVPK cells were inoculated in the 6-well cell culture plate with 3 ml of MEM supplemented with 5% fetal calf serum in the incubator containing 5% CO, at 37° C. When the cells grew to half-full, the following solutions were prepared: solution A, by adding 1 mg of pKS/CMV-SVDV-T or pCI/SVDV-T into 100 ml of OPTI-MEM (GIBCO BRL); and solution B, by dissolving 20 ml of lipofectin (GIBCO BRL) with 100 ml of OPTI-MEM. After mixing solutions A and B, the mixture was left at room temperature for 15 minutes. The half-full cells were washed with 1×PBS twice. Then, 0.8 ml of OPTI-MEM was added into each well, and the solutions of mixing A with B which had been left for 15 minutes was added. The transfected MVPK cells were left in the incubator for 16 hours. The cells were then washed with 1×PBS and 3 ml of MEM broth supplemented with 5% fetal calf serum was added. The cells were returned to the incubator. After 24 hours, it was observed that obvious plaques were formed, as shown in FIG. 6(a). After 24 more hours, it was observed that the MVPK cells were completely lyzed by the virus, as shown in FIG. 6(b). However, the MVPK cells of the control (MVPK cells transfected with pKS/CMV or pCI) grew to full. 3 ml of the viral cytolyzing solution was used to infect the MVPK cells cultured in 3 ml of MEM supplemented with 5% fetal calf serum that had grown to full. After 16 hours, obvious plaques were observed. Therefore, it was confirmed that the transfection of MVPK cell with expression plasmids of SVDV such as pKS/CMV-SVDV-T and pCI/SVDV-T produced infectious SVDV. The cultivation of virus was according to the method described in Example 1. The titer of the viral cytolyzing solution, the titer of the purified virus, and the density of the virus after gradient centrifugation were all the same as the parental SVDV.

Figure 8:
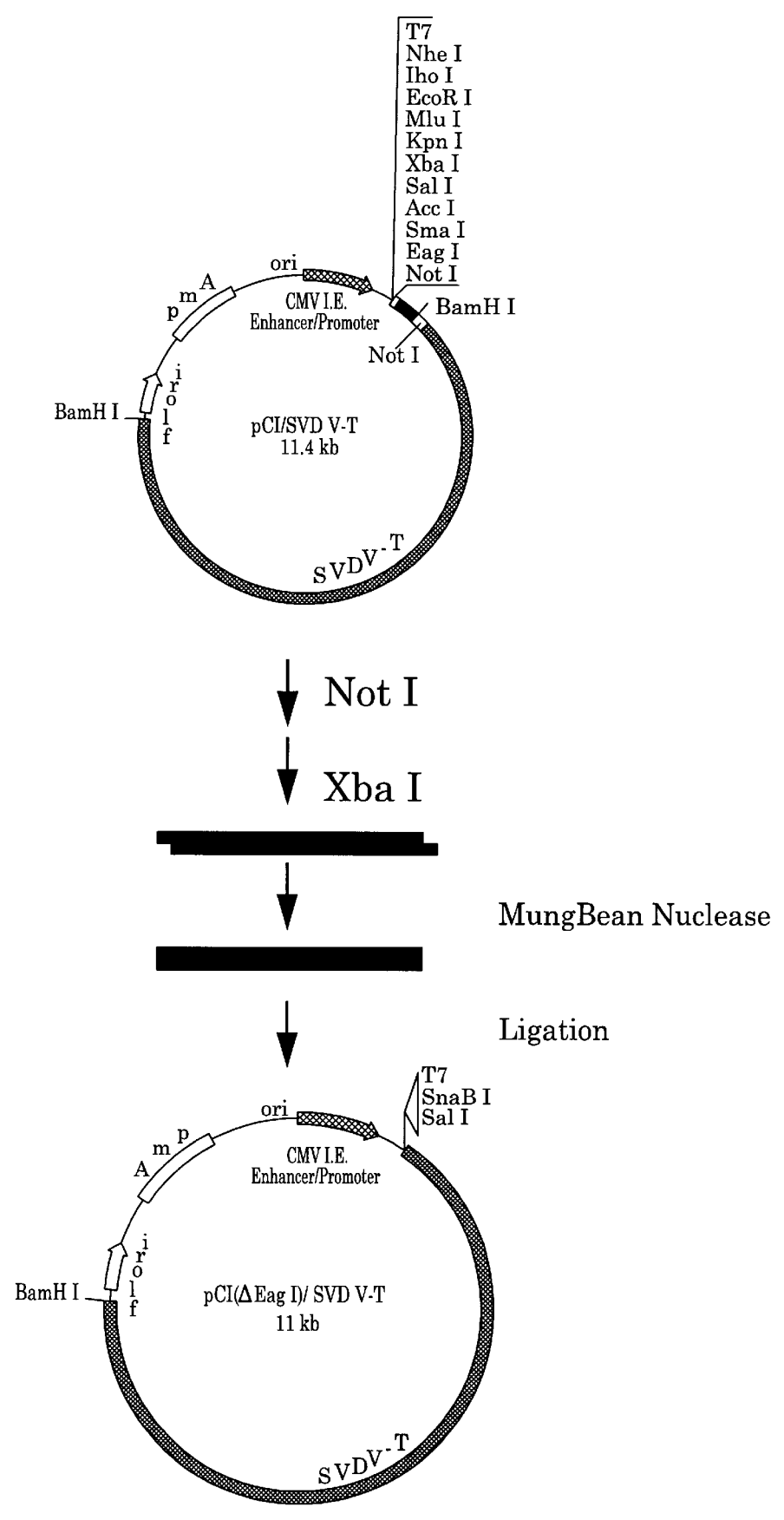

Example 5
Preparation of the expression plasmid of mutant strains of SVDV
(1) Construction of plasmid pCI (Δ Eag I)/SVDV-T
Expression plasmid pCI (Δ Eag I)/SVDV-T was constructed as shown in FIG. 8.
The purpose to construct plasmid pCI (Δ Eag I)/SVDV-T is to remove the Eag I site in the pCI vector so that the Eag I site at position 1442 bp SVDVcDNA can be used to construct mutant strains. Plasmid pCI/SVDV-T was digested with Not I and Xho I restriction endonucleases at 37° C. for 2 hours. After purification, the plasmid DNA was treated with 15 units/50 ml of Munge Bean nuclease (New England Biolabs) at 25° C. for 30 minutes. DNAs were separated with 0.8% agarose gel electrophoresis. About 11.5 kb the fragment was cut. After purification, the ends of the fragment were ligated to each other with T4 ligase. The ligation mixture was used to transform E. Coli DH5α strain. After plasmid preparation, the plasmid DNA was digested with Eag I restriction endonuclease at 37° C. for 2 hours. After analyzing with 0.8% agarose gel electrophoresis, about 11.5 kb linear plasmid that was only cut at one site was selected. After the subsequent DNA sequencing, it was confirmed that the EagI site in the vector was removed and the construction of plasmid pCI (Δ Eag I)/SVDV-T was prepared. The restriction map of the plasmid is shown in FIG. 9.

(2) Construction of plasmid pCI (Δ Eag I)/SVDV-T (Δ Sph I)
Expression plasmid pCI (Δ Eag I)/SVDV-T (Δ Sph I) was constructed as shown in FIG. 9.
The purpose to construct plasmid pCI (Δ Eag I)/SVDV-T (Δ Sph I) is to remove the Sph I restriction site at position 6772 bp cDNA of SVDV, so that the Sph I at position 2660 bp becomes the only Sph I restriction site in the entire plasmid and can be used for the construction of mutant strains. The 5900–7300 bp cDNA fragment of SVDV was prepared by the method of overlap extension PCR (Gene, 77, 51–59 (1989)). The DNA sequence of the Sph I site at position 6772 bp was changed to GTGGC by primer design. The encoding amino acid residues remained the same but the Sph I restriction site was deleted. The resulting cDNA fragment was then used to displace the corresponding fragment in pCI (Δ Eag I)/SVDV-T by the Nsi I restriction site at position 6345 bp and the Cla I restriction site at position 6928 to construct pCI (Δ Eag I)/SVDV-T (Δ Sph I). The detailed steps of the construction were as follows. The plasmid pCI (Δ Bag I)/SVDV-T was used as a template. SVDV5900 (+) and SVDV6760-Sph I (−) were used as a pair of PCR primers. Another PCR used SVDV6760-Sph I(−) and SVDV7300 (−) as the primers. PCR reaction mixture contained 10 μl of 10×ExTaq buffer, 8 μl of 2.5 mM dNTPs, 0.2 μg of each primer, 0.05 μg of the template, 0.5 μl of ExTaq (TaKaRa), and water added to a final volume of 100 μl. The PCR reaction conditions were 1 cycle of 94° C. for 1 minute, 30 cycles consisting of 94° C. for 30 seconds, 50° C. for 30 seconds and 72° C. for 1 minutes, and followed by 1 cycle of 72° C. for 3 minutes. After completion of the reaction, the PCR product was analyzed with 0.8% agarose gel electrophoresis. It was clearly observed that the former primer pair produced a DNA product of about 870 bp and the later primer pair produced a DNA product of about 530 bp. These DNA fragments were cut. After purification, 0.05 μg of the 870 bp and 530 bp DNA fragments were used respectively as templates to perform PCRs with 0.2 μg each of SVDV5900 (+) and SVDV7300 (−) as the primer pair, 10 μl of 10×ExTaq buffer, 8 μl of 2.5 mM dNTPs, 0.5 μl of ExTaq and water added to a final volume of 100 μl. The PCR reaction conditions were 1 cycle of 94° C. for 1 minute, 30 cycles consisting of 94° C. for 30 seconds, 56° C. for 30 seconds and 72° C. for 1.5 minutes, and followed by 1 cycle of 72° C. for 3 minutes. After completion of the reaction, the PCR product was analyzed by 0.8% agarose gel electrophoresis. A DNA fragment at the position of 1.5 kb was clearly observed. The 1.5 kb DNA fragment was cut off. After purification, the fragment was digested with Nsi I and Cal I restriction endonucleases at 25 37° C. for 90 minutes. DNAs were separated by 0.8% agarose gel and about 0.5 kb DNA fragment was cut. After purification, the fragment was stored at 4° C. Plasmid pCI (Δ Eag I)/SVDV-T was also digested with Nsi I and Cal I restriction endonucleases at 37° C. for 2 hours. DNAs were separated by 0.8% agarose gel and about 11 kb DNA fragment was cut. After purification, the 11 kb DNA fragment was ligated to the 0.5 kb DNA fragment with T4 DNA ligase at 16° C. for 16 hours. The ligation mixture was used to transform E. Coli DH5α strain. After isolating plasmid, the plasmid containing only one Sph I restriction site was selected by Sph I restriction endonuclease. With the subsequent DNA sequencing, the construction of plasmid pCI (Δ Eag I)/SVDV-T (Δ Sph I) was confirmed. The restriction map of the plasmid is shown in FIG. 11.

The sequence of the primers are as follows:

```
SVDV5900 (+):        GAA ATG TTT AGG GAG TAC AAT CAC [SEQ ID NO: 9]
                     AGA CAC AGC

SVDV6760-Sph I (-):  AGC ATC CTG ATG GCA TAC CGC CCC [SEQ ID NO:10]
                     TCA CAA

SVDV6760-Sph I (+):  TTG TGA GGG GCG GTA TGC CAT CAG [SEQ ID NO:11]
                     GAT GCT

SVDV7300 (-):        TTA AAA GGA GTC CAA CCA CTT CCT [SEQ ID NO:12]
```

(3) Construction of plasmid pCI (Δ Eag I, Δ Hind III)/ SVDV-T (Δ Sph I)

Expression plasmid pCI (Δ Eag I, Δ Hind III)/SVDV-T (Δ Sph I) was constructed as shown in FIG. 12.

Figure 13:
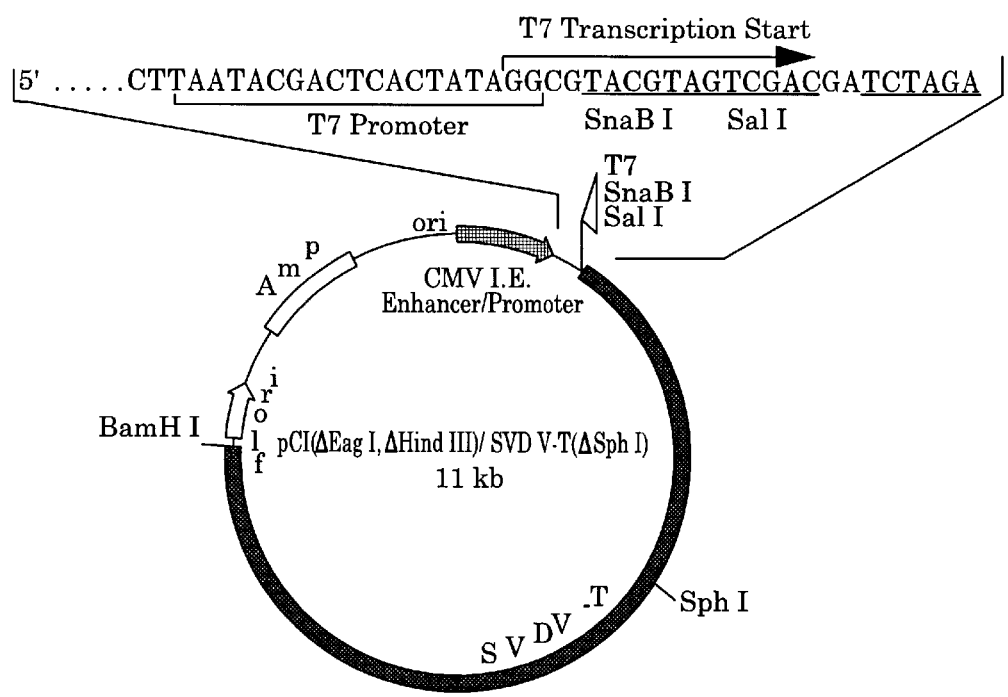
FIG. 13 is a diagram illustrating a restriction map of the plasmid pCI(Δ Eag I, Δ Hind III)/SVDV-T(Δ Sph I) (including SEQ ID NO:32).

The purpose to construct plasmid pCI (Δ Eag I, Δ Hind III)/SVDV-T (Δ Sph I) is to remove the Hind III site in the vector to facilitate the construction of SVDV mutant strains of SVDV. Plasmid pCI (Δ Eag I)/SVDV-T (Δ Sph I) was digested by Hind III restriction endonuclease. The ends of the digested plasmid were then made up with Klenow enzyme. After purification, the ends were ligated to each other with T4 DNA ligase. The ligation mixture was used to transform E. Coli DH5α strain. After isolating plasmid, the plasmid DNA was digested with Hind III restriction endonuclease at 37° C. for 2 hours. After analyzing with 0.8% agarose gel, the plasmid without cut was selected. After the subsequent DNA sequencing confirming the deletion of the Hind III site, the construction of plasmid pCI (Δ Eag I, Δ Hind III)/SVDV-T (Δ Sph I) was prepared. The restriction map of the plasmid is shown in FIG. 13.

(4) Construction of expression plasmid of mutant strain of SVDV, pCI (Δ Eag I, Δ Hind III)/SVDV-T (Δ Sph I)/H21

Figure 14:
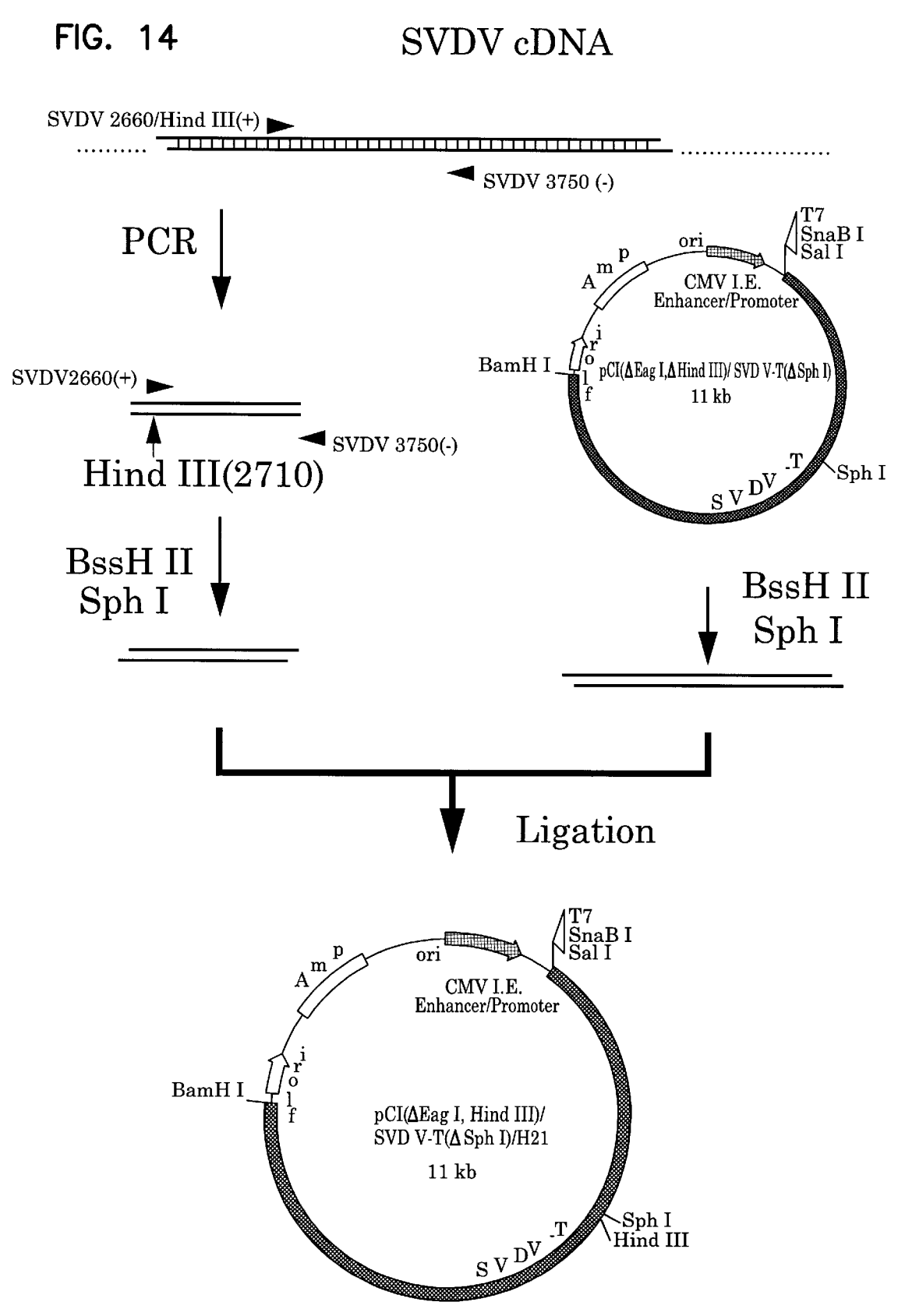

The expression plasmid of mutant strain of SVDV, pCI (Δ Eag I, Δ Hind III)/SVDV-T (Δ Sph I)/H21, was constructed as shown in FIG. 14.

Figure 15:
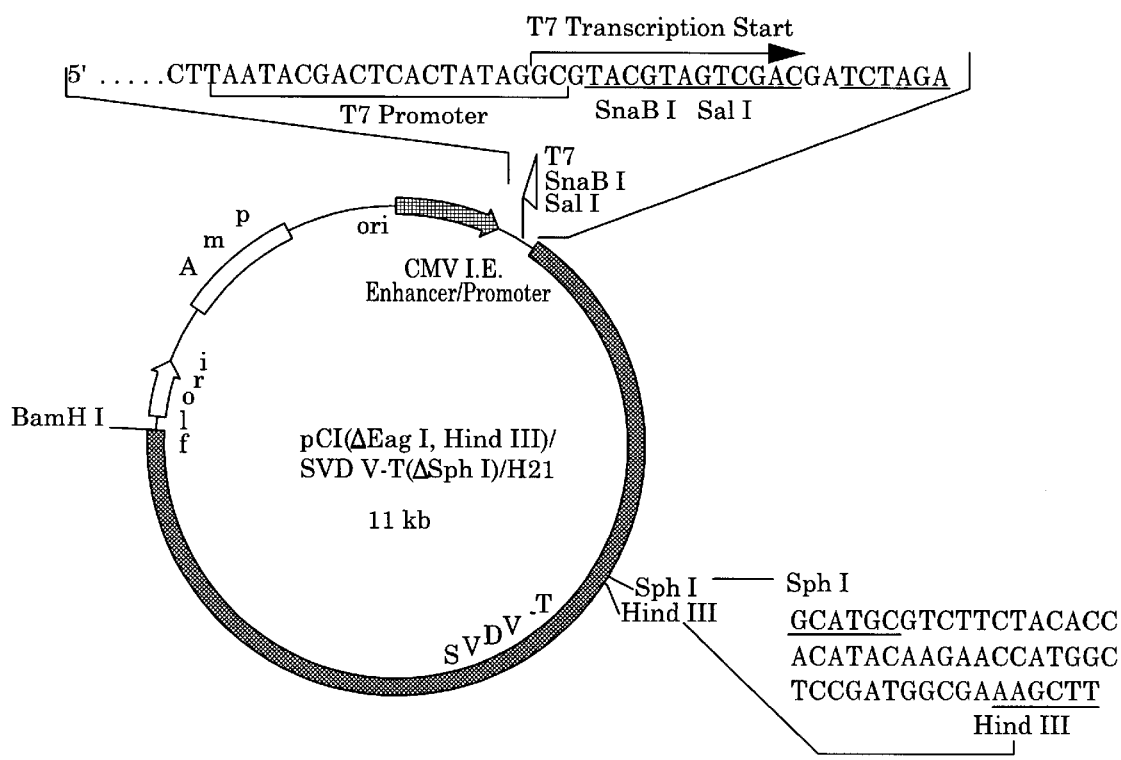
FIG. 15 is a diagram illustrating a restriction map of the plasmid pCI(Δ Eag I, Δ Hind III)/SVDV-T(Δ Sph I)/H21 (including SEQ ID NO:32–33).

The purpose to construct plasmid pCI (Δ Eag I, Δ Hind III)/SVDV-T (L Sph I)/H21 is to introduce a Hind III restriction site at position 2710 bp of SVDV. The site can form a gene replacement cassette with the Sph I restriction site at position 2660 bp. The DNA sequence between 2600 and 2710 bp of SVDVcDNA can therefore be easily altered by cassette displacement. In addition, with the introduction of the Hind III restriction site, the 87 and 88 amino acid residues of VP1 can also be changed from DN to ES to produce a mutant strain of SVDV. The 2660–3750 bp DNA fragment of SVDV was prepared by PCR. The Hind III restriction endonuclease sequence was introduced to the 2710 bp position by primer design (SVDV2660/Hind III 2710). The reaction mixture containing 0.1 1μg of SVDV 2660/Hind III-2710 and SVDV 3750 (−) primer pair, 10 μl of 10×ExTaq buffer, 8 μl of 2.5 mM dNTPs, 0.5 μl of ExTaq and water was added to a final volume of 100 μl. The PCR reaction conditions were 1 cycle of 94° C. for 1 minute, 30 cycles consisting of 94° C. for 30 seconds, 54° C. for 1 minute and 72° C. for 75 seconds, and followed by a cycle of 72° C. for 2.5 minutes. After completion of the reaction, the PCR product was separated by 0.8% agarose gel, and the 1.1 kb DNA fragment was cut. After purification, the fragment was digested with BssH II restriction endonuclease at 50° C. for 2 hours, purified, digested with Sph I restriction endonuclease at 37° C. for 16 hours, and then stored at 4° C. The 3370–2660 bp DNA fragment of SVDV in plasmid pCI (Δ Eag I, Δ Hind III)/SVDV-T (A Sph I) was removed using BssH II and Sph I restriction endonucleases under the reaction conditions same as above. The PCR product and plasmid treated with BssH II and Sph I restriction endonucleases were separated by 0.8% agarose gel. A 0.71 kb DNA fragment was cut off from the lane of the PCR product and a 10 kb DNA fragment was cut from the lane of the plasmid. After purification, the two fragments were ligated with T4 DNA ligase at 16° C. The ligation mixture was used to transform E. Coli DH5α strain. Plasmids were isolated from each colony and the plasmids that can be digested by Hind III restriction endonuclease to form linear DNA molecules were selected. After the subsequent DNA sequencing confirming the existence of the Hind III restriction sequence at position 2710 bp, the construction of expression plasmid pCI (Δ Eag I, Δ Hind III)/SVDV-T (Δ Sph I)/H21 was prepared. The restriction map of the plasmid is shown in FIG. 15. According to the method of Example 4, the expression plasmid produced infectious mutant strain H21 of SVDV.

Primer DNA sequences:

```
SVDV2660/Hind III (+):  GTG CAC ATC TGC ATG CGT CTT CTA [SEQ ID NO:13]
                        CAC CAC ATA CAA GAA CCA TGG
                        CTC CGA TGG CGA AAG CTT CGC SVDV3750 (-):           TCC TTG CTC CAT GGC GTC GTC CTC [SEQ ID NO:14]
                        CAG CCA CAA
```

(5) Construction of expression plasmid of mutant strain of SVDV, pCI (Δ Eag I, Δ Hind III)/SVDV-T (Δ Sph I)/SP7

Figure 16:
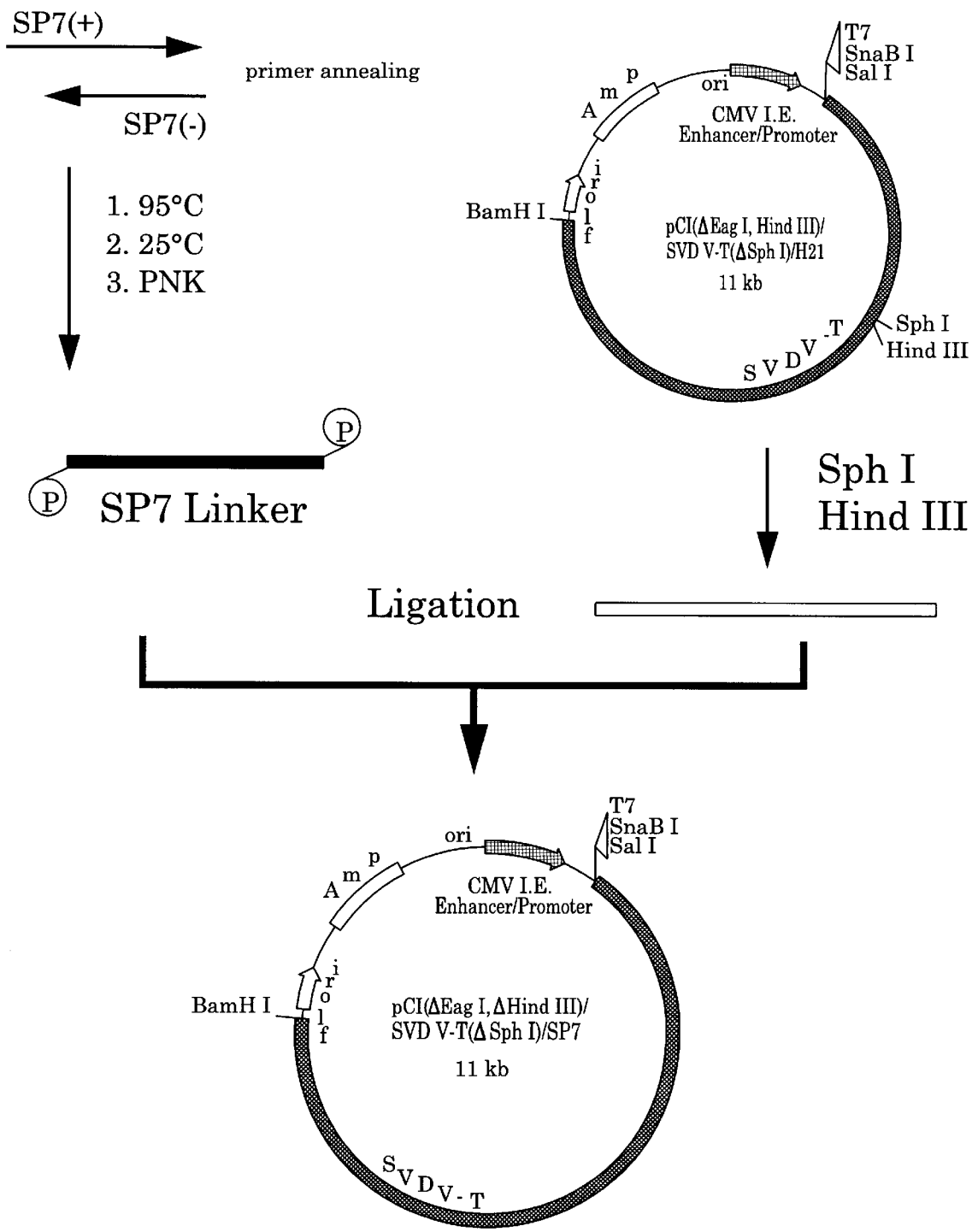
FIG. 16 is a diagram illustrating a construction of the plasmid pCI(Δ Eag I, Δ Hind III)/SVDV-T(Δ Sph I)/SP7.

The expression plasmid of a mutant strain of SVDV, pCI (Δ Eag I, Δ Hind III)/SVDV-T (Δ Sph I)/SP7, was constructed as shown in FIG. 16.

The purpose to construct this plasmid is to displace the 85–88 amino acid sequence of VP1 protein of SVDV. That is, the sequences are changed from DGDN to TTNKDKS. Said this region is the epitope of VP1. Therefore, the mutant strain with the mutation on epitope of VP1 can be prepared.

Figure 17:
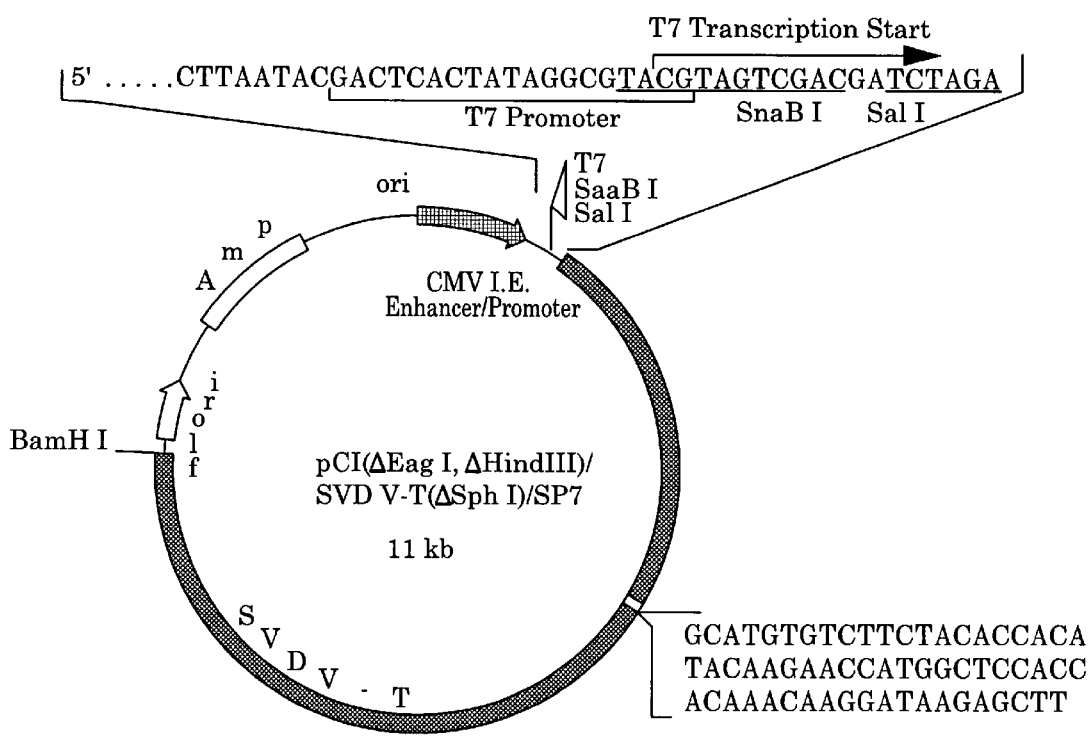
FIG. 17 is a diagram illustrating a restriction map of the plasmid pCI(Δ Eag I, Δ Hind III)/SVDV-T(Δ Sph I)/SP7 (including SEQ ID NO: 32–34).
Figure 18:
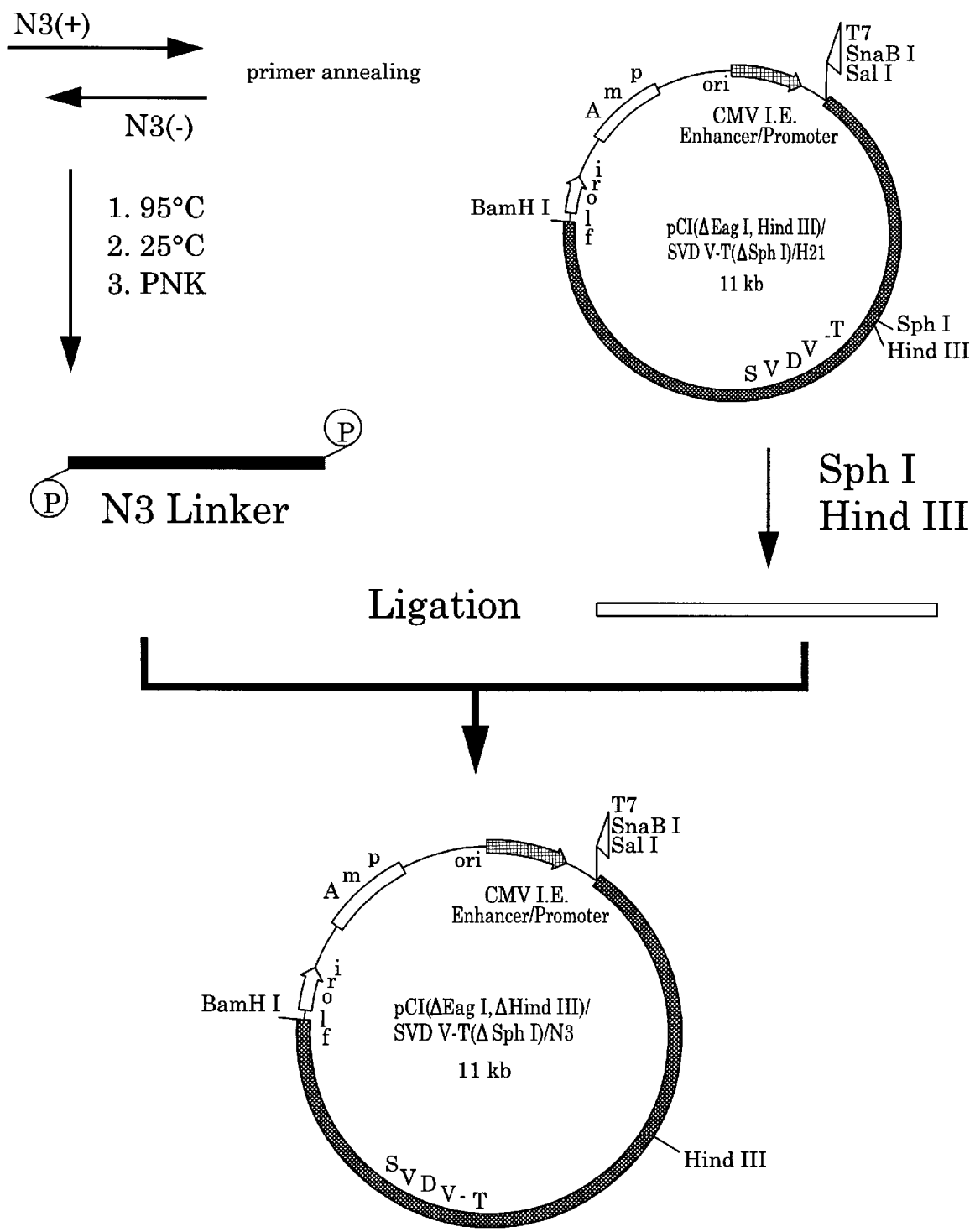
FIG. 18 is a diagram illustrating a construction of the plasmid pCI(Δ Eag I, Δ Hind III)/SVDV-T(Δ Sph I)/N3.

The construction procedure was as follows. The 2660–2710 DNA fragment of plasmid pCI (Δ Eag I, Δ Hind III)/SVDV-T (Δ Sph I)/H21 was cut using Sph I and Hind III restriction endonucleases at 37° C. for 2 hours. DNAs were separated with 0.8% agarose gel. About 10 kb DNA fragment was cut, purified, and stored at 4° C. Then, 5 μg of the SP7(+) and SP7(-) polynucleotides were dissolved in 100 μl of 2.5 mM Tris-HCl (pH 6.8). The solution was heated to 95° C. for 5 minutes and then cooled at room temperature for 30 minutes to allow the annealing of the SP7(+) and SP7(-) polynucleotides. After purification, 2 μl of 10×PNK buffer, 1 μl of polynucleotide phosphorylase (PNK, NEB), and 1 μl of 2.5 mM ATP were added to 1 μg of the annealing product. The reaction was performed at 37° C. for 30 minutes. After purification, the reaction product was ligated to the 10 kb DNA fragment with T4 DNA ligase at 16° C. The ligation mixture was used to transform *E. Coli* DH5α strain. Plasmids were isolated from each colony and treated with Hind III restriction endonuclease. After analyzing with 0.8% agarose gel, the plasmids that cannot be digested by Hind III restriction endonuclease were selected. After the subsequent DNA sequencing confirming the correct DNA sequence of the replacement region, the construction of expression plasmid pCI (Δ Eag I, Δ Hind III)/SVDV-T (Δ Sph I)/SP7 was prepared. The restriction map of the plasmid is shown in FIG. 17. According to the method of Example 4, MVPK cells are transfected with the plasmid to produce infectious mutant strain SP7 of SVDV. DNA sequences:

```
SP7(+):  TGT CTT CTA CAC CAC ATA CAA GAA CCA TGG CTC   [SEQ ID NO:15]
         CAC CAC AAA CAA GGA TAA G

SP7(-):  AGC TCT TAT CCT TGT TTG TGG TGG AGC CAT GGT   [SEQ ID NO:16]
         TCT TGT ATG TGG TGT AGA AGA CAC ATG
```

(6) Construction of expression plasmid of mutant strain of SVDV. pCI (Δ Eag I, Δ Hind III)/SVDV-T (L Sph I)/N3

The expression plasmid of mutant strain of SVDV, pCI (Δ Eag I, Δ Hind III)/SVDV-T (Δ Sph I)/N3, was constructed as shown in FIG. 16.

Figure 19:
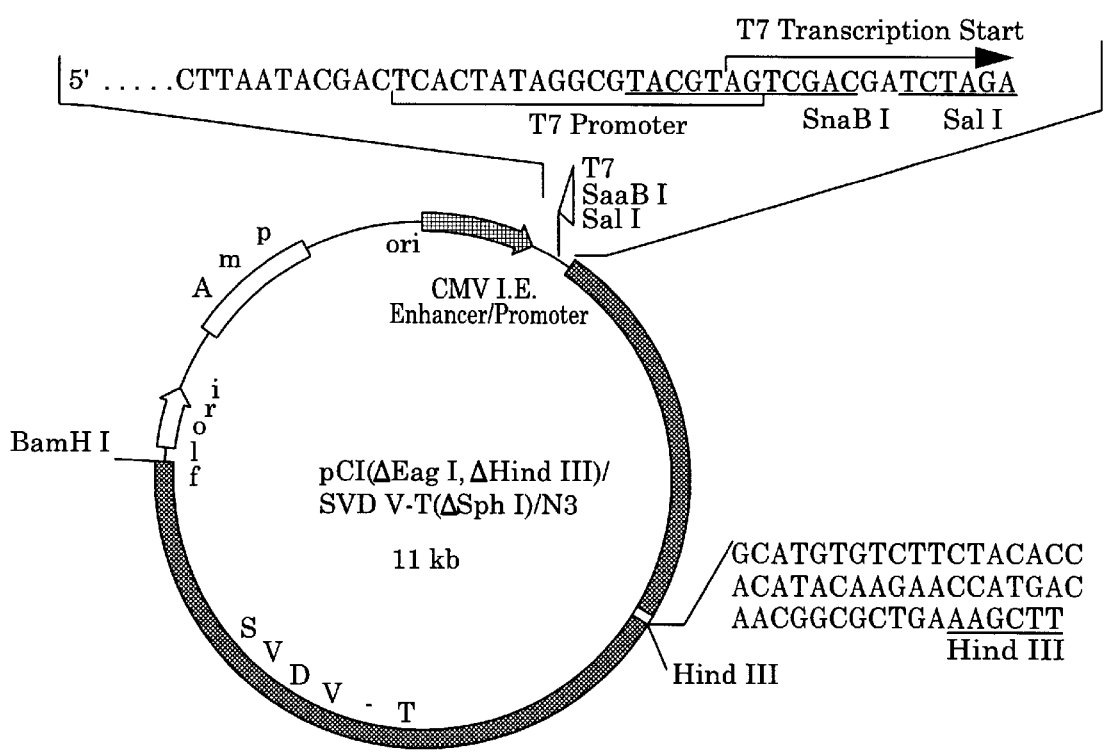
FIG. 19 is a diagram illustrating a restriction map of the plasmid pCI(Δ Eag I, Δ Hind III)/SVDV-T(Δ Sph I)/N3 (including SEQ ID NO: 32 and 35).

The purpose to construct this plasmid is to displace the 85–88 amino acid sequence of VP1 protein of SVDV. That is, the sequences are changed from DGDN to GAES. The construction process was conducted as described in Example 5(5), except that the N3(±) polynucleotides were used instead of SP7(±) polynucleotides. The plasmids to be selected can be digested by Hind III restriction endonuclease rather than by Sph I restriction endonuclease. After the subsequent DNA sequencing confirming the correct DNA sequence of the replacement region, the construction of expression plasmid pCI (Δ Eag I, Δ Hind III)/SVDV-T (Δ Sph I)/N3 was prepared. The restriction map of the plasmid is shown in FIG. 19. According to the method of Example 4, MVPK cells are transfected with the plasmid to produce infectious SVDV mutant strain N3 of SVDV.

DNA sequences:

```
N3(+):  TGT CTT CTA CAC CAC ATA CAA GAA CCA TGA CAA
        CGG CGC TGA A [SEQ ID NO:17]

N3(-):  AGC TTT CAG CGC CGT TGT CAT GGT TCT TGT ATG
        TGG TGT AGA AGA CAC ATG [SEQ ID NO:18]
```

Figure 20:
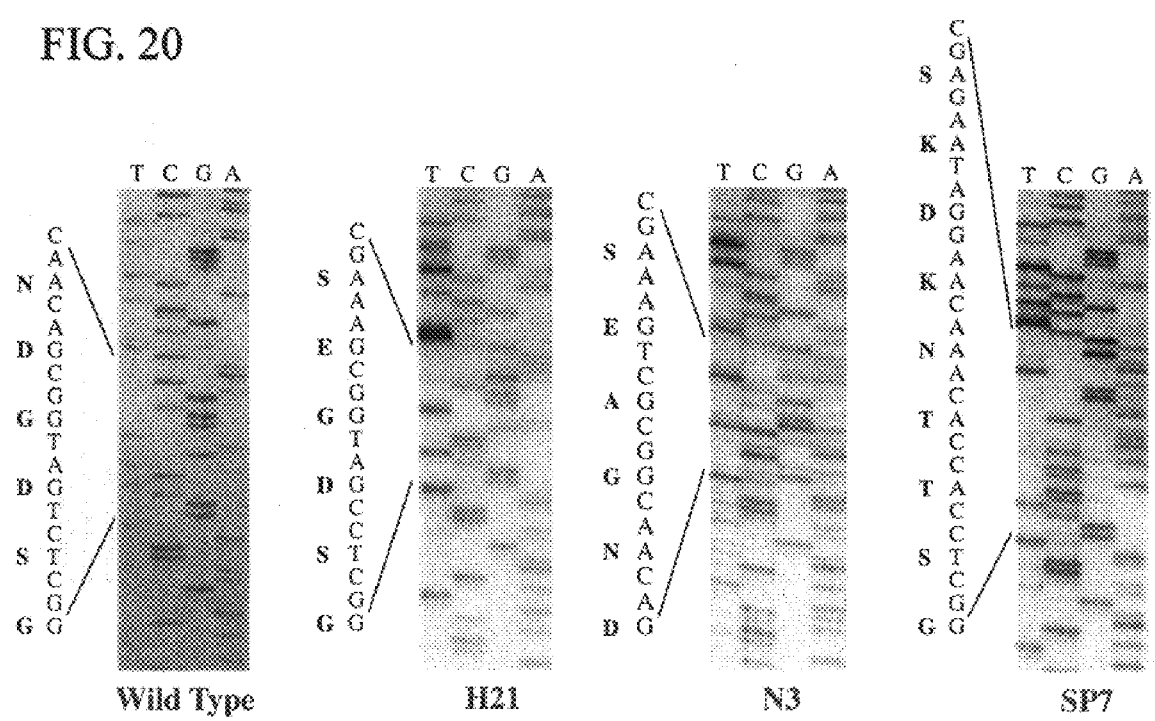
FIG. 20 is a diagram illustrating the nucleotide sequences of the mutant sites for the mutant strains H21, SP7 and N3 of SVDV (including SEQ ID NO: 36–39).

Example 6. DNA sequencing of the gene displacement region of mutant strains of SVDV The use of DNA sequencing confirms the correct displaced nucleotides in the antigen determinant region of the mutants. To 1 μl of the viral cDNA of the mutant strains (RT-PCR was performed as above), 5 μl of 10X PCR buffer, 0.25 mM dNTPs, 0.1 μg each of oligonucleotide primers of SVDV: SVD 3296 (-) [AGT GGT TTT CAT GGT TGT TAT ATC] [SEQ ID NO: 19] and SVD 2500 (+) [GGA AGA GCC ATT GCC CGC GTC GCT GAT ACC ATT] [SEQ ID NO: 20] and water to a total volume of 50 μl were added. One unit of Klen Taq (LA Technology) was then added. After quick spin, mineral oil was added. The reaction was incubated at 94° C. for 1 minute, followed by 30 cycles consisting of 94° C. for 30 seconds, 54° C. for 30 seconds and 72° C. for 1 minute, and followed by 72° C. for 3 minutes. A double-stranded cDNA fragment of 706 bp was obtained. The DNA fragment obtained was then separated by 0.8% agarose gel electrophoresis, purified, and used for sequencing (DNA sequencing reagents were purchased from TOYOBO Co. LTD). To 11 μl of the purified DNA fragment, 3 μl of the reaction solution, 0.2 μg/μl of oligonucleotide primer of SVDV: SVD 2600 (+): AGA CAC GTG AAG AAT TAC CAT, [SEQ ID NO: 21] 0.75 μl of dNTP, 1 unit of Δ Tth polymerase, 10 μci [a-$^{35}$S]dATP and water to a total volume of 17 μl were added. After quick spin, 4 μl of the reaction mixture was added into each of the eppendorfs marked as A, G, C and T. Then, 2 μl of ddA, ddG, ddC and ddT was added respectively. After adding mineral oil, the eppendorfs were incubated in the heating block of 95° C. for 5 minutes. By that time, the eppendorfs were immediately cooled on ice for 2 minutes and then subjected to 30 cycles consisting of 95° C. for 30 seconds and 72° C. for 2 minutes. Four μl of the quenching reagent was added to stop the reaction. After heating the sequencing reaction to 90° C. for 2 minutes, electrophresis analysis was performed on 6% sequencing gel. After X-ray autoradiography, the nucleotide sequence was determined. The result is shown in FIG. 20.

Example 7

Differentiation of the mutant strains of SVDV from wild-type strain of SVDV by reverse transcription-polymerase chain reaction (RT-PCR)

Figure 21:
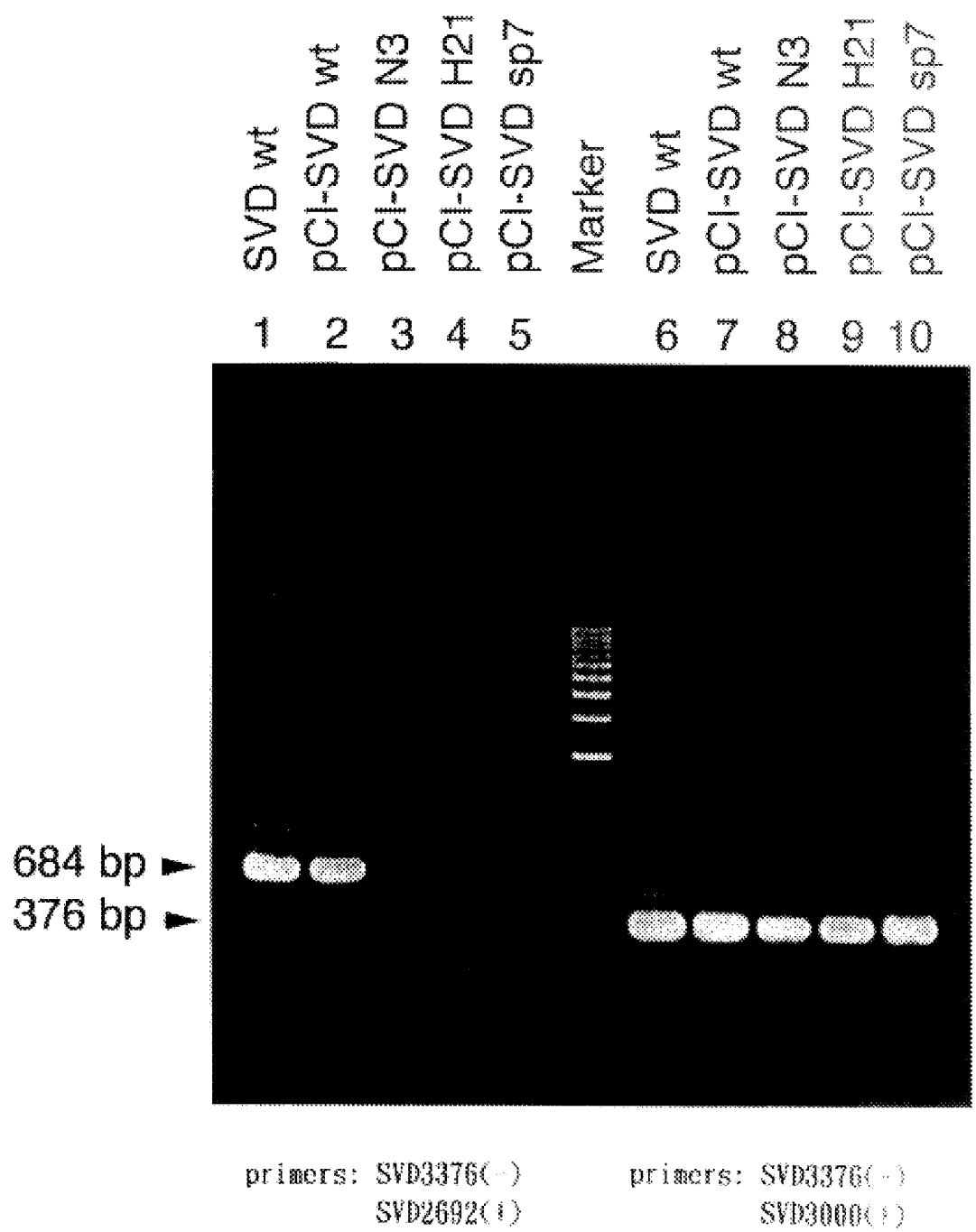
FIG. 21 is a diagram illustrating a differentiation of the mutant strains of swine vesicular disease virus from wild type strain of SVDV by reverse transcriptase—polymerase chain reaction (RT-PCR).

To develop an identification method for the differentiation from wild-type strain of SVDV, RT-PCR was used with the nucleotide primers within the gene displacement region of the epitope of SVDV. The TRIZOL reagents (Gibco BRL) were used to prepare the RNAs of the wild type strain and mutant strains of SVDV. Then, the use of RT-PCR prepare the cDNAs of SVDV as follows. To 5 μl of the viral RNA extracted as above, 50 mM Tris-HCl (pH 8.3), 75 mM KCl, 3 mM MgCl$_2$, 10 mM DTT, 12.5 mM dNTPs, 0.2 μg of primer of SVDV: SVDV 3376 (−), 14 units of nuclease inhibitor, 100 μ M-MLV reverse transcriptase and water to a total reaction volume of 50 μl were added. The reaction was incubated at 37° C. for 75 minutes. After inactivation of the enzyme by incubating the reaction at 80° C. for 5 minutes, the first strand cDNA was obtained. To 1 μl of the 10-fold diluted first strand cDNA, 5 μl of 10×PC2 buffer, 500 mM Tris-HCl (pH 9.1), 35 mM MgCl$_2$, 12.5 mM dNTPs, a pair of oligonucleotide primers of SVDV: 0.1 μg each of SVDV 3376 (−) and SVDV 2692 (+) for the test group, or 0.1 μg each of SVDV 3376 (−) and SVDV 3000 (+) for the control group and water to a total volume of 50 ml were added. One unit of Klen Tag (LA Technology) was then added. After quick spin, mineral oil was added. PCR reaction was incubated at 94° C. for 1 minute, followed by 30 cycles consisting of 94° C. for 30 seconds, 54° C. for 30 seconds and 72° C. for 1 minute, and followed by 72° C. for 3 minutes. Double-stranded cDNA fragment of various sizes were obtained, as shown in FIG. 21. The PCR product on the right of 1 kb DNA marker was prepared by the primer pair of SVDV 3376 (−) and SVDV 3000 (+). Since the sequences at the positions of the primers were not altered in the mutant strains (samples 8, 9 and 10), the mutants had the same 376 bp DNA fragment as the wild type strains (samples 6 and 7). The PCR product on the left of 1 kb DNA marker was prepared by the primer pair of SVDV 3376 (−) and SVDV 2692 (+). Since the sequence at the position of primer SVDV 2692(+) was changed in the mutant strains (samples 3, 4 and 5), no PCR product was obtained. On the contrary, the wild type strains (samples 6 and 7) produced a 684 bp DNA fragment. Therefore, the use of RT-PCR, the mutant and wild type strains of SVDV can be distinguished by the suitable designs of the primers.

Primer sequences are as follows:

```
SVDV3375 (-):    TCC GCG CGC GTT GCG AGA       [SEQ ID NO:22]

SVDV2999 (+):    ATT GGC ATA GGC AAC GCA TAC   [SEQ ID NO:23]

SVDV2692 (+):    TGG CTC TGA TGG CGA CAA       [SEQ ID NO:24]
```

Example 8
The ability of the inactivated vaccine of SVDV in inducing neutralization antibody produced by mice
(1) Immunization of mice with SVDV
Wild type strain was cultured and purified as described in Example 1. The mutant strains N3, SP7 and H21 of SVDV with a concentration of 25 μg or 50 μg of protein per 0.75 μl were added to 2.4 mM BEI solution. The mixtures were stirred in the incubator at 37° C. After inactivation for 24 hours, 2.4 mM Na$_2$S$_2$O$_3$ was added to each mixture to neutralize the toxicity of BEI. An equal volume of Freund's adjuvant was added to form a toothpaste-like mixture. 10 μg each of the inactivated vaccines of SVDV was subcutaneously injected to each group of three 6-week-old mice (BALB/C, purchased from the Center of Animal Experiments National Taiwan University). Immunization was performed every two weeks for three times. Blood samples were collected before each immunization and after two weeks of the third immunization. The blood samples were precipitated by standing and centrifuged to produce serum samples. 0.1 M BEI was prepared as follows: 4.32 g of NaOH was added to 600 ml of H$_2$O and stirred until completely dissolved. Then, 1.23 g of 2-bromoethylamine HBr was then added and stirred until completely dissolved. The solution was filtered through a 0.2 mm sterile filter and the preparation of 0.1 M BEI was done.

(2) Determination of the serum neutralization antibody
A cell suspension containing 500,000 MVPK cells was added to a 96-well microtiter plate. The plate was incubated in the incubator under 5% $CO_2$ at 37° C. for 2 hours to allow that the MVPK cells can attach to the microtiter plate and the culture solution was then removed.

Fifty pi of the mouse serum samples were first diluted to 10 folds in the eppendorfs. Then, the equal amounts of 2-fold serial dilution were then performed. Each dilution was conducted on 4 wells. Equal amounts of 2.5 virus/50 μl of SVDV solution were then added and the mixtures were incubated in the incubator under 5% $CO_2$ at 37° C. for 60 minutes. The mixtures of virus and serum were transferred to the microtiter plate wherein the cells have been attached and the plate was then incubated in-the incubator under 5% $CO_2$ at 37° C. for 48 to 72 hours. When cytopathic effect (CPE) appeared on the cells in the viral solution. the results were read. The titers of the serum neutralization antibody in the serum samples obtained after two weeks of the third immunization are shown in Table 1. No neutralization antibody was detected in the serum obtained from the three mice of the control group. The serum samples of the mice immunized with the wild type strain and the N3, SP7 and H21 mutant strains of SVDV contained neutralization antibodies. As to the lowest titers, all the mutant strains were higher than the wild type strain. With respect to the highest titers, except for the titer of H21 equal to the wild type strain, the titers of N3 and SP7 were higher than the wild type strain. Therefore, it can be concluded that mice immunized with the mutant strains disclosed by the present invention can produce neutralization antibodies, and the titers produced by the mutant strains are higher than that by the wild type strain.

TABLE 1

Efficacy of mice immunized with SVDV to produce neutralization antibody

| SVDV strains | titer |
| --- | --- |
| control | 0 |
|  | 0 |
|  | 0 |
| wild-type strain | 40 |
|  | 80 |
|  | 160 |
|  | 160 |
|  | 640 |
| H21 strain | 160 |
|  | 320 |
|  | 320 |
|  | 640 |
|  | 640 |
| N3 strain | 640 |
|  | 640 |
|  | 1280 |
|  | 2560 |
|  | 2560 |
| SP7 strain | 80 |
|  | 320 |

TABLE 1-continued

Efficacy of mice immunized with SVDV to produce neutralization antibody

| SVDV strains | titer |
|---|---|
| | 640 |
| | 640 |
| | 1280 |

SEQUENCE LISTING

<160> NUMBER OF SEQ ID NOS: 39

<210> SEQ ID NO 1
<211> LENGTH: 7400
<212> TYPE: DNA
<213> ORGANISM: SWINE VESICULAR DISEASE VIRUS

<400> SEQUENCE: 1

```
ttaaaacagc ctgtgggttg ttcccaccca cagggcccac tgggcgctag cacactggta    60
tcacggtacc tttgtgcgcc tgtttgactt accctcccca aacgcaactt agaagcacaa   120
cttaaatggt caatagacgg ctcagtatgc caactgagtc tcgatcaagc acttctgtta   180
ccccggactg agtaccaata ggctgctcac ccggctgaag gggaaaccgt tcgttacccg   240
actaactact tcgagaaacc tagtaccacc atgaaagttg cgcacgtttc gttccgcaca   300
accccagtgt agatcaggcc gatgagtcac cccaaacccc acgggcgacc gtggcggtgg   360
ctgcgctggc ggcctgccca tgggcaaact catgggatgc ttcaatactg acatggtgcg   420
aagagtctat tgagctagtt ggtagtcctc cggcccctga atgcggctaa tcctaactgc   480
ggagcagata cccacgcacc agtgggcagt ctgtcgtaat gggcaactct gcagcggaac   540
cgactacttt gggtgtccgt gtttcctttt gttcttatac tggctactta tggtgacaat   600
tgagagattg taaccatatt gctattggat tggccacctg cgacgaata  gaacagttgc   660
ttacctgttt gttggtctcg tatcactgaa ctacaaagcc ttaaacaccc tttaatttca   720
tcataacgct caatacgtta aaatgggagc tcaagtgtca acacaaaaga ccggtgctca   780
tgagaccagc ttgagtgcag cgggcaactc agtcattcat tacacaaaca taaactacta   840
caaggatgct gcttcaaatt cagcaaatag acaagacttc acacaggacc cggggaagtt   900
caccgaacct gtgaaagaca tcatggtcaa atcatcgcct gctctcaatt ccccatcagc   960
agaggagtgt ggctacagtg acagggtaag atccatcacc ttagggaatt cgaccataac  1020
aactcaagaa tgtgcaaacg tggtagttgg atatgggggtg tggccaactt acttgaagga  1080
tgaagaggca acagcagagg atcaacccac tcaaccagat gtggccacgt gcaggtttta  1140
cacgctcgaa tccgtgatgt ggcaacagag ttcaccaggc tggtggtgga agttccctga  1200
cgcgttgtcc aacatgggc tatttgggca aaatatgcag taccactacc ttgggagagc  1260
cggatacacg atacacgtgc agtgcaacgc gtccaaattt caccaagggt gtctgctggt  1320
ggtatgtgtg ccagaagcag agatgggggtg tgccacgttg gccaataagc ctgacccaaa  1380
aagcctgagt aaaggggaaa tagccaacat gtttgaatcc caaagctcca ccggggaaac  1440
ggccgtgcaa gctaatgtga tcaatgcagg catgggtgtt ggtgttggta atctaactat  1500
```

```
cttcccccac cagtggatca acttgcgcac taacaacagc gctacgattg tcatgccata    1560
tataaacagc gtgcccatgg acaacatgtt cagacacaac aattttacac tcatggtcat    1620
cccgttcgcc ccactgagct acagcacagg ggctaccacg tacgtaccaa tcactgtgac    1680
agtggcgcca atgtgcgctg aatataatgg gctgcgtctg gccggcaagc aaggtttacc    1740
aacgctgtcg acacccggga gcaaccagtt tctcacgtcc gatgacttcc agtcaccatc    1800
agccatgcca caattcgatg tcactcctga gatggatatt ccaggacaag tcaacaactt    1860
gatggagatt gcagaagtag attctgtagt gcctgtaaac aacacagaag ggaaagtgat    1920
gtcaattgag gcataccaga tacctgtgca atcgaatcca accaacggtt ctcaggtttt    1980
tgggttccca ttgaccccag gggccaatag tgtgttaaac aggactttgc tgggagaaat    2040
cttaaactac tatgcccatt ggtcaggcag catcaaacta acatttatgt tttgcgggtc    2100
agcgatggct acaggaaaat tcttactggc atactcacca ccgggagctg gggcaccgac    2160
cacacgcaag gaggcgatgc taggtactca cgtgatctgg gatgtgggtc tacaatcgag    2220
ctgcgtattg tgtataccat ggattagtca aacgcactac aggtatgtag taatggatga    2280
atacaccgct ggtggataca taacttgctg gtatcaaaca aatattgtgg tgcctgcaga    2340
tgcacagagt gactgtaaga tcttgtgttt tgtgtcggca tgtaacgatt tctcagttag    2400
gatgctcaag gacacaccct ttataaaaca ggataatttc ttccaagggc ccccaggaga    2460
ggtgatggaa agagccgttg cccgcgtcgc tgataccatt gggagcggac cagttaactc    2520
ggaatccatt ccagctctaa ccgccgcaga gacagggcac acgtcacaag ttgtaccatc    2580
agacacaatg caaactaggc acgtgaagaa ttatcattca aggtcagagt cgacagtgga    2640
gaacttcctg tgcagatctg catgcgtctt ctacaccaca tacaagaacc atggctctga    2700
tggcgacaac ttcgcctact gggtaatcaa cacacggcaa gttgctcaac tgcgtcggaa    2760
gctcgaaatg ttcacgtacg caagatttga tctggagttg accttcgtga tcactagcac    2820
tcaggaacaa cccaccgtta aggtcaaga tacaccagtg ctcacccacc aaataatgta    2880
tgtacctcca ggtggtccag tacccacaaa ggtaaacagc tacagctggc aaacgtccac    2940
caacccaagt gtgttctgga cggaagggag cgcaccgcct cgaatgtcga tactattcat    3000
tggcataggc aacgcataca gcatgttcta tgacgggtgg gccaggtttg acaagcaagg    3060
gacatacgcc gtccaagcac taaacaacat ggggacacta tatatgagac atgtgaatga    3120
tgggggtccc ggtccattg tgagcacagt acgaattac ttcaagccaa agcacgtcaa    3180
aacgtgggtc ccaagaccgc ccagactatg tcaataccaa aaggctggca acgtgaattt    3240
tgaacccact ggtgtgactg agggtaggac agatataaca accatgaaaa ccactggcgc    3300
cttcgggcag cagtctggtg ccgtgtacgt tggcaactat agagtggtga atagacatct    3360
cgcaacgcgc gcggactggc aaaactgtgt gtgggaagac tacaacagag accttctagt    3420
gagcaccacc actgcacatg gctgcgacac cattgccagg tgcgattgca cagcaggagt    3480
gtacttctgc gcctccagaa acaagcacta tccagtcaca tttgagggc ccggtcttgt    3540 gaaggttcaa gagagtgagt attacccgaa aaagtaccaa tcccatgtac tgctcgcagc    3600
tggatttgca gagccggtg attgtggagg gattctcaga tgccaacatg gggtgattgg    3660
catagttacc gtgggggggg aaggtgttgt tggttttgcc gatgtaagag acttgttgtg    3720
gctggaggac gatgccatgg agcaaggagt tagggattat gtggaacaac tcggcaactg    3780
cttcggctca ggattcacca atcaaatttg cgaacaggtt acccttctaa aagagtcgtt    3840
```

```
aattggacag gattctatcc ttgagaagtc tctcaaggcc ctcgtcaaga tagtatcagc   3900
actcgtgatc gtggtgagaa atcacgatga cctcattacg gtcaccgcca cactggcgtt   3960
aataggatgt accacctcac catggcgctg gctcaagcag aaagtgtctc agtactatgg   4020
catccccatg gctgaaaggc aaaatagtgg ctggttaaag aagttcacag agatgaccaa   4080
tgcctgtaag ggcatggagt ggatagccat caagatccaa aaattcatag agtggttgaa   4140
ggttaagatc ctgccagaag tcaaggaaaa gcatgagttc ctcaacaggc ttaaacaact   4200
accactcttg gaaagtcaaa tagcaactat tgagcagagt gcaccatctc aaagtgacca   4260
ggagcaacta ttctctaatg tacagtactt tgcccactac tgtcggaagt atgcaccatt   4320
gtacgccgct gaagcaaaga gagtgttctc acttgaaaag aagatgagca attacataca   4380
gttcaagtcc aaatgccgta ttgaacccgt ctgtctcttg ctccatggca gcccaggcgc   4440
tgggaagtct gtggcaacga acttgattgg gcgctcgctc gctgagaaac tcaacagctc   4500
ggtgtactca ctaccaccag atccagacca tttcgatggt tacaaacagc aagctgttgt   4560
catcatggac gacttgtgcc agaacccgga cggtaaagat gtgtccttgt tctgtcagat   4620
ggtctccagc gttgacttcg tgcctcccat ggcggcgctt gaggaaaaag gcattctatt   4680
cacctcgccg ttcgttctcg cgtccaccaa tgcagggtca gttaacgccc ccacggtctc   4740
cgacagtaga gcactcgtaa gaaggttcca ttttgacatg aacatcgagg ttatttccat   4800
gtatagccag aacggtaaga tcaacatgcc tatggcagtt aaaacatgtg atgaggagtg   4860
ttgcccggtc aacttcaaaa agtgctgccc actagtgtgt ggcaaagcta tacaattcat   4920
agacaggagg acccaagtta ggtattcatt ggacatgctg gttaccgaaa tgtttaggga   4980
gtacaatcac acacacagtc tgggggccac cctcgaggca ttgttccaag gaccaccagt   5040
ttatagagag atcaaaatca gtgttgcccc agaaactcct ccaccaccag cagttgccga   5100
cttactaaaa tcagtagaca gtgaggctgt gagggagtac tgcaaggaga aaggtggct    5160 tataccagag gtcgattcca ccctacagat agaaaagcat gtgagcagag cgttcatatg   5220
tttgcaagct ctaaccacat ttgtctcggt tgcaggcata atatacatca tctacaaatt   5280
gtttgcaggt ttccaaggcg catacacagg gatgcctaat cagaagccca aggtgcccac   5340
cctgagacaa gccaaagtgc aggtccagc gtttgagttc gccgtggcga tgatgaaaag   5400
aaacgccagt acagtgaaaa ctgagtatgg tgaattcacc atgcttggga tttacgacag   5460
gtgggcggtt tgccacgcc atgccaaacc tggccccacc atcttgatga acgaccaggt   5520
agtcggagtg ttggacgcca aggaactagt tgataaagat gggaccaacc tggaattgac   5580
tctcttgaag ctcaaccgca acgagaagtt tagagacatc aggggattct tagcacgaga   5640
ggaggtcgaa gtgaacgaag ctgtcctagc aataaacaca agtaaattcc cgaatatgta   5700
catacccgtg ggccgggtaa ccgactatgg gttcttaaat ctgggtggaa ccccacgaa    5760 gagaatgctc atgtacaatt tcccaactag ggcaggccag tgtggggtg tccttatgtc    5820 aacagggaaa gtcctgggaa tacatgtagg agggaatgga caccaagggt ttcagcggc    5880 actcctcaga cactacttca atgaggagca gggtgagata gaattcattg agagctcaaa   5940
ggacgcagga tttcccgtga tcaacactcc cagcaagaca aaaattggaa caagtgtgtt   6000
tcaccacgtg ttcgagggca caaggaacc agcggttctc agaaatgggg acccacgact   6060
caaggccaac tttgaggagg caatcttctc caagtacatt ggcaatgtta acacacatgt   6120
agacgagtac atgatggagg ctgtagatca ttatgcagga caactagcca cactggacat   6180
cagcacggaa cccatgaagc tagaagatgc cgtgtatggc actgagggggc tcgaagcact   6240
```

```
agacctgacc accagtgcag gttaccctta tgtggccctg ggtatcaaga aaagagacat    6300
cctatccaag aagaccagag accttaccaa gctaaaggaa tgcatggaca aatatggtct    6360
aaacttgcca atggtaacct atgtcaagga cgagttgaga tctgccgaca aagtggccaa    6420
gggaaaatcc aggctcatcg aggcttctag cctcaacgac tcagtagcaa tgaggcagac    6480
atttggaaac ctatataaga ctttccacct caacccgggc atcgttacgg gtagcgccgt    6540
tgggtgtgac ccagatgtct tttggagcaa gatccccgtt atgctcgatg gacatgtcat    6600
agcgtttgac tattcaggct atgacgccag cctcagccca gtgtggttta cgtgcttgaa    6660
actcctcctg gagaagctag ggtacacaaa caaggaaacg aactacatag actacctctg    6720
taattcccac cacctgtaca gggacaaaca ctactttgtg aggggcggca tgccatcagg    6780
atgctcaggc actagcatat ttaattccat gattaacaac atcataatca gaaccctcat    6840
gctgaaggtt tataaaggca ttgatttgga ccaattcaga atgattgcat atggggatga    6900
tgtgatagct tcatacccgt ggcccatcga tgcctcactg ctagctgaag cagggaagga    6960
ttgtggcttg atcatgaccc cagcagataa aggcgagtgt ttcaatgagg taacctggac    7020
aaacatgacc ttcctgaaaa ggtacttcag gcagatgaa cagtacccat ttttggtcca    7080
tcctgtcatg ccaatgaagg atatacacga atccattagg tggactaaag atcctaagaa    7140
cacacaggat cacgtgcgct cgctgtgttt attggcttgg cacaacgggg agcacgaata    7200
tgaggagttt attcgtaaga tcagaagcgt gcccgtaggg cgctgcttgt ccctccctgc    7260
gttttcaacg ctgcgcagga agtggttgga ctccttttaa aattagagca caattagtca    7320
atcataattg gctcaaccct accgcatgaa ccgaacttga taaaagtgcg gtagggtaa    7380 attctccgta ttcggtgcgg                                                 7400
```

<210> SEQ ID NO 2
<211> LENGTH: 1220
<212> TYPE: DNA
<213> ORGANISM: SWINE VESICULAR DISEASE VIRUS

<400> SEQUENCE: 2

```
ttaaaacagc ctgtgggttg ttcccaccca cagggcccac tgggcgctag cacactggta     60
tcacggtacc tttgtgcgcc tgtttgactt accctcccca aacgcaactt agaagcacaa    120
cttaaatggt caatagacgg ctcagtatgc caactgagtc tcgatcaagc acttctgtta    180
ccccggactg agtaccaata ggctgctcac ccggctgaag gggaaaccgt tcgttacccg    240
actaactact tcgagaaacc tagtaccacc atgaaagttg cgcacgtttc gttccgcaca    300
accccagtgt agatcaggcc gatgagtcac cccaaacccc acgggcgacc gtggcggtgg    360
ctgcgctggc ggcctgccca tgggcaact catgggatgc ttcaatactg acatggtgcg    420
aagagtctat tgagctagtt ggtagtcctc cggcccctga atgcggctaa tcctaactgc    480
ggagcagata cccacgcacc agtgggcagt ctgtcgtaat gggcaactct gcagcggaac    540
cgactacttt gggtgtccgt gtttccttt gttcttatac tggctactta tggtgacaat    600
tgagagattg taaccatatt gctattggat tggccacctg gcgacgaata gaacagttgc    660
ttacctgttt gttggtctcg tatcactgaa ctacaaagcc ttaaacaccc tttaatttca    720
tcataacgct caatacgtta aaatgggagc tcaagtgtca acacaaaaga ccggtgctca    780
tgagaccagc ttgagtgcag cggcaactc agtcattcat tacacaaaca taaactacta    840
caaggatgct gcttcaaatt cagcaaatag acaagacttc acacaggacc cggggaagtt    900
```

```
caccgaacct gtgaaagaca tcatggtcaa atcatcgcct gctctcaatt ccccatcagc    960
agaggagtgt ggctacagtg acagggtaag atccatcacc ttagggaatt cgaccataac   1020
aactcaagaa tgtgcaaacg tggtagttgg atatggggtg tggccaactt acttgaagga   1080
tgaagaggca acagcagagg atcaacccac tcaaccagat gtggccacgt gcaggtttta   1140
cacgctcgaa tccgtgatgt ggcaacagag ttcaccaggc tggtggtgga agttccctga   1200
cgcgttgtcc aacatggggc                                               1220

<210> SEQ ID NO 3
<211> LENGTH: 6
<212> TYPE: DNA
<213> ORGANISM: SWINE VESICULAR DISEASE VIRUS

<400> SEQUENCE: 3 gaaagc                                                                 6

<210> SEQ ID NO 4
<211> LENGTH: 18
<212> TYPE: DNA
<213> ORGANISM: SWINE VESICULAR DISEASE VIRUS

<400> SEQUENCE: 4
gacaacggcg ctgaaagc                                                   18

<210> SEQ ID NO 5
<211> LENGTH: 27
<212> TYPE: DNA
<213> ORGANISM: SWINE VESICULAR DISEASE VIRUS

<400> SEQUENCE: 5
ggctccacca caaacaagga taagagc                                         27

<210> SEQ ID NO 6
<211> LENGTH: 32
<212> TYPE: DNA
<213> ORGANISM: SWINE VESICULAR DISEASE VIRUS

<400> SEQUENCE: 6
gctctagatt aaaacagcct gtgggttgtt cc                                   32

<210> SEQ ID NO 7
<211> LENGTH: 9
<212> TYPE: DNA
<213> ORGANISM: SWINE VESICULAR DISEASE VIRUS

<400> SEQUENCE: 7 cgggatcct                                                              9

<210> SEQ ID NO 8
<211> LENGTH: 21
<212> TYPE: DNA
<213> ORGANISM: SWINE VESICULAR DISEASE VIRUS

<400> SEQUENCE: 8
attaatacga ctcactatag g                                               21

<210> SEQ ID NO 9
<211> LENGTH: 33
<212> TYPE: DNA
<213> ORGANISM: SWINE VESICULAR DISEASE VIRUS

<400> SEQUENCE: 9
```

-continued

```
gaaatgttta gggagtacaa tcacagacac agc                           33

<210> SEQ ID NO 10
<211> LENGTH: 30
<212> TYPE: DNA
<213> ORGANISM: SWINE VESICULAR DISEASE VIRUS

<400> SEQUENCE: 10
agcatcctga tggcataccg cccctcacaa                               30

<210> SEQ ID NO 11
<211> LENGTH: 30
<212> TYPE: DNA
<213> ORGANISM: SWINE VESICULAR DISEASE VIRUS

<400> SEQUENCE: 11
ttgtgagggg cggtatgcca tcaggatgct                               30

<210> SEQ ID NO 12
<211> LENGTH: 24
<212> TYPE: DNA
<213> ORGANISM: SWINE VESICULAR DISEASE VIRUS

<400> SEQUENCE: 12
ttaaaaggag tccaaccact tcct                                     24

<210> SEQ ID NO 13
<211> LENGTH: 66
<212> TYPE: DNA
<213> ORGANISM: SWINE VESICULAR DISEASE VIRUS

<400> SEQUENCE: 13
gtgcacatct gcatgcgtct tctacaccac atacaagaac catggctccg atggcgaaag    60
cttcgc                                                         66

<210> SEQ ID NO 14
<211> LENGTH: 33
<212> TYPE: DNA
<213> ORGANISM: SWINE VESICULAR DISEASE VIRUS

<400> SEQUENCE: 14
tccttgctcc atggcgtcgt cctccagcca caa                           33

<210> SEQ ID NO 15
<211> LENGTH: 52
<212> TYPE: DNA
<213> ORGANISM: SWINE VESICULAR DISEASE VIRUS

<400> SEQUENCE: 15
tgtcttctac accacataca agaaccatgg ctccaccaca aacaaggata ag      52

<210> SEQ ID NO 16
<211> LENGTH: 60
<212> TYPE: DNA
<213> ORGANISM: SWINE VESICULAR DISEASE VIRUS

<400> SEQUENCE: 16
agctcttatc cttgtttgtg gtggagccat ggttcttgta tgtggtgtag aagacacatg    60

<210> SEQ ID NO 17
<211> LENGTH: 43
<212> TYPE: DNA
```

<213> ORGANISM: SWINE VESICULAR DISEASE VIRUS

<400> SEQUENCE: 17
tgtcttctac accacataca agaaccatga caacggcgct gaa    43

<210> SEQ ID NO 18
<211> LENGTH: 51
<212> TYPE: DNA
<213> ORGANISM: SWINE VESICULAR DISEASE VIRUS

<400> SEQUENCE: 18
agctttcagc gccgttgtca tggttcttgt atgtggtgta agagacacat g    51

<210> SEQ ID NO 19
<211> LENGTH: 24
<212> TYPE: DNA
<213> ORGANISM: SWINE VESICULAR DISEASE VIRUS

<400> SEQUENCE: 19
agtggttttc atggttgtta tatc    24

<210> SEQ ID NO 20
<211> LENGTH: 33
<212> TYPE: DNA
<213> ORGANISM: SWINE VESICULAR DISEASE VIRUS

<400> SEQUENCE: 20
ggaagagcca ttgcccgcgt cgctgatacc att    33

<210> SEQ ID NO 21
<211> LENGTH: 21
<212> TYPE: DNA
<213> ORGANISM: SWINE VESICULAR DISEASE VIRUS

<400> SEQUENCE: 21
agacacgtga agaattacca t    21

<210> SEQ ID NO 22
<211> LENGTH: 18
<212> TYPE: DNA
<213> ORGANISM: SWINE VESICULAR DISEASE VIRUS

<400> SEQUENCE: 22
tccgcgcgcg ttgcgaga    18

<210> SEQ ID NO 23
<211> LENGTH: 21
<212> TYPE: DNA
<213> ORGANISM: SWINE VESICULAR DISEASE VIRUS

<400> SEQUENCE: 23
attggcatag gcaacgcata c    21

<210> SEQ ID NO 24
<211> LENGTH: 18
<212> TYPE: DNA
<213> ORGANISM: SWINE VESICULAR DISEASE VIRUS

<400> SEQUENCE: 24
tggctctgat ggcgacaa    18

<210> SEQ ID NO 25
<211> LENGTH: 160

```
<212> TYPE: DNA
<213> ORGANISM: SWINE VESICULAR DISEASE VIRUS

<400> SEQUENCE: 25
ggatccggtg gtggtgcaaa tcaaagaact gctcctcagt ggatgttgcc tttacttcta      60
ggcctgtacg gaagtgttac ttctgctcta aaagctgcgg aattgtaccc gcggccgcta     120
atacgactca ctatagggcg tacgtagtcg acgatctaga                           160

<210> SEQ ID NO 26
<211> LENGTH: 40
<212> TYPE: DNA
<213> ORGANISM: SWINE VESICULAR DISEASE VIRUS

<400> SEQUENCE: 26
cttaatacga ctcactatag gctagcctcg agaattcacg                            40

<210> SEQ ID NO 27
<211> LENGTH: 40
<212> TYPE: DNA
<213> ORGANISM: SWINE VESICULAR DISEASE VIRUS

<400> SEQUENCE: 27
cgtggtacct ctagagtcga cccgggcggc cgcttcgagc                            40

<210> SEQ ID NO 28
<211> LENGTH: 240
<212> TYPE: DNA
<213> ORGANISM: SWINE VESICULAR DISEASE VIRUS

<400> SEQUENCE: 28
agacatgata agatacattg atgagtttgg acaaaccaca actagaatgc agtgaaaaaa      60
atgctttatt tgtgaaattt gtgatgctat tgctttattt gtaaccatta taagctgcaa     120
taaacaagtt aacaacaaca attgcattca ttttatgttt caggttcagg gggagatgtg     180
ggaggttttt taaagcaagt aaaacctcta caaatgtggt aaaatcgata aggatccggt     240

<210> SEQ ID NO 29
<211> LENGTH: 80
<212> TYPE: DNA
<213> ORGANISM: SWINE VESICULAR DISEASE VIRUS

<400> SEQUENCE: 29
ggtggtgcaa atcaaagaac tgctcctcag tggatgttgc ctttacttct aggcctgtac      60
ggaagtgtta cttctgctct                                                  80

<210> SEQ ID NO 30
<211> LENGTH: 40
<212> TYPE: DNA
<213> ORGANISM: SWINE VESICULAR DISEASE VIRUS

<400> SEQUENCE: 30
aaaagctgcg gaattgtacc cgcggccgct aatacgactc                            40

<210> SEQ ID NO 31
<211> LENGTH: 31
<212> TYPE: DNA
<213> ORGANISM: SWINE VESICULAR DISEASE VIRUS

<400> SEQUENCE: 31
actatagggc gtacgtagtc gacgatctag a                                     31
```

<210> SEQ ID NO 32
<211> LENGTH: 43
<212> TYPE: DNA
<213> ORGANISM: SWINE VESICULAR DISEASE VIRUS

<400> SEQUENCE: 32
cttaatacga ctcactatag gcgtacgtag tcgacgatct aga            43

<210> SEQ ID NO 33
<211> LENGTH: 53
<212> TYPE: DNA
<213> ORGANISM: SWINE VESICULAR DISEASE VIRUS

<400> SEQUENCE: 33
gcatgcgtct tctacaccac atacaagaac catggctccg atggcgaaag ctt    53

<210> SEQ ID NO 34
<211> LENGTH: 62
<212> TYPE: DNA
<213> ORGANISM: SWINE VESICULAR DISEASE VIRUS

<400> SEQUENCE: 34
gcatgtgtct tctacaccac atacaagaac catggctcca ccacaaacaa ggataagagc    60
tt                                                                   62

<210> SEQ ID NO 35
<211> LENGTH: 53
<212> TYPE: DNA
<213> ORGANISM: SWINE VESICULAR DISEASE VIRUS

<400> SEQUENCE: 35
gcatgtgtct tctacaccac atacaagaac catgacaacg gcgctgaaag ctt    53

<210> SEQ ID NO 36
<211> LENGTH: 18
<212> TYPE: DNA
<213> ORGANISM: SWINE VESICULAR DISEASE VIRUS

<400> SEQUENCE: 36
caacagcggt agtctcgg                                        18

<210> SEQ ID NO 37
<211> LENGTH: 18
<212> TYPE: DNA
<213> ORGANISM: SWINE VESICULAR DISEASE VIRUS

<400> SEQUENCE: 37
cgaaagcggt agcctcgg                                        18

<210> SEQ ID NO 38
<211> LENGTH: 18
<212> TYPE: DNA
<213> ORGANISM: SWINE VESICULAR DISEASE VIRUS

<400> SEQUENCE: 38
cgaaagtcgc ggcaacag                                        18

<210> SEQ ID NO 39
<211> LENGTH: 27

-continued

<212> TYPE: DNA
<213> ORGANISM: SWINE VESICULAR DISEASE VIRUS

<400> SEQUENCE: 39
cgagaatagg aacaaacacc acctcgg                27

What is claimed is:

1. An isolated DNA molecule encoding the full genome of the Taiwan Yu-Li strain of SVDV, which comprises the sequence of SEQ ID NO: 1, as follows:

```
                                         (SEQ ID NO:1)
1     TTAAAACAGC CTGTGGGTTG TTCCCACCCA CAGGGCCCAC

TGGGCGCTAG

51    CACACTGGTA TCACGGTACC TTTGTGCGCC TGTTTGACTT

ACCCTCCCCA

101   AACGCAACTT AGAAGCACAA CTTAAATGGT CAATAGACGG

CTCAGTATGC

151   CAACTGAGTC TCGATCAAGC ACTTCTGTTA CCCCGGACTG

AGTACCAATA

201   GGCTGCTCAC CCGGCTGAAG GGGAAACCGT TCGTTACCCG

ACTAACTACT

251   TCGAGAAACC TAGTACCACC ATGAAAGTTG CGCACGTTTC

GTTCCGCACA

301   ACCCCAGTGT AGATCAGGCC GATGAGTCAC CCCAAACCCC

ACGGGCGACC

351   GTGGCGGTGG CTGCGCTGGC GGCCTGCCCA TGGGGCAACT

CATGGGATGC

401   TTCAATACTG ACATGGTGCG AAGAGTCTAT TGAGCTAGTT

GGTAGTCCTC

451   CGGCCCCTGA ATGCGGCTAA TCCTAACTGC GGAGCAGATA

CCCACGCACC

501   AGTGGGCAGT CTGTCGTAAT GGGCAACTCT GCAGCGGAAC

CGACTACTTT

551   GGGTGTCCGT GTTTCCTTTT GTTCTTATAC TGGCTACTTA

TGGTGACAAT

601   TGAGAGATTG TAACCATATT GCTATTGGAT TGGCCACCTG

GCGACGAATA

651   GAACAGTTGC TTACCTGTTT GTTGGTCTCG TATCACTGAA

CTACAAAGCC

701   TTAAACACCC TTTAATTTCA TCATAACGCT CAATACGTTA

AAATGGGAGC

751   TCAAGTGTCA ACACAAAAGA CCGGTGCTCA TGAGACCAGC

TTGAGTGCAG

801   CGGGCAACTC AGTCATTCAT TACACAAACA TAAACTACTA

CAAGGATGCT

851   GCTTCAAATT CAGCAAATAG ACAAGACTTC ACACAGGACC

CGGGGAAGTT

901   CACCGAACCT GTGAAAGACA TCATGGTCAA ATCATCGCCT

GCTCTCAATT

951   CCCCATCAGC AGAGGAGTGT GGCTACAGTG ACAGGGTAAG

ATCCATCACC

1001  TTAGGGAATT CGACCATAAC AACTCAAGAA TGTGCAAACG

TGGTAGTTGG

1051  ATATGGGGTG TGGCCAACTT ACTTGAAGGA TGAAGAGGCA

ACAGCAGAGG

1101  ATCAACCCAC TCAACCAGAT GTGGCCACGT GCAGGTTTTA

CACGCTCGAA

1151  TCCGTGATGT GGCAACAGAG TTCACCAGGC TGGTGGTGGA

AGTTCCCTGA

1201  CGCGTTGTCC AACATGGGGC TATTTGGGCA AAATATGCAG

TACCACTACC

1251  TTGGGAGAGC CGGATACACG ATACACGTGC AGTGCAACGC

GTCCAAATTT

1301  CACCAAGGGT GTCTGCTGGT GGTATGTGTG CCAGAAGCAG

AGATGGGGTG

1351  TGCCACGTTG GCCAATAAGC CTGACCCAAA AAGCCTGAGT

AAAGGGGAAA

1401  TAGCCAACAT GTTTGAATCC CAAAGCTCCA CCGGGGAAAC

GGCCGTGCAA

1451  GCTAATGTGA TCAATGCAGG CATGGGTGTT GGTGTTGGTA

ATCTAACTAT

1501  CTTCCCCCAC CAGTGGATCA ACTTGCGCAC TAACAAVAGC

GCTACGATTG

1551  TCATGCCATA TATAAACAGC GTGCCCATGG ACAACATGTT

CAGACACAAC
```

-continued

```
1601 AATTTTACAC TCATGGTCAT CCCGTTCGCC CCACTGAGCT
     ACAGCACAGG
1651 GGCTACCACG TACGTACCAA TCACTGTGAC AGTGGCGCCA
     ATGTGCGCTG
1701 AATATAATGG GCTGCGTCTG GCCGGCAAGC AAGGTTTACC
     AACGCTGTCG
1751 ACACCCGGGA GCAACCAGTT TCTCACGTCC GATGACTTCC
     AGTCACCATC
1801 AGCCATGCCA CAATTCGATG TCACTCCTGA GATGGATATT
     CCAGGACAAG
1851 TCAACAACTT GATGGAGATT GCAGAAGTAG ATTCTGTAGT
     GCCTGTAAAC
1901 AACACAGAAG GGAAAGTGAT GTCAATTGAG GCATACCAGA
     TACCTGTGCA
1951 ATCGAATCCA ACCAACGGTT CTCAGGTTTT TGGGTTCCCA
     TTGACCCCAG
2001 GGGCCAATAG TGTGTTAAAC AGGACTTTGC TGGGAGAAAT
     CTTAAACTAC
2051 TATGCCCATT GGTCAGGCAG CATCAAACTA ACATTTATGT
     TTTGCGGGTC
2101 AGCGATGGCT ACAGGAAAAT TCTTACTGGC ATACTCACCA
     CCCGGGAGCTG
2151 GGGCACCGAC CACACGCAAG GAGGCGATGC TAGGTACTCA
     CGTGATCTGG
2201 GATGTGGGTC TACAATCGAG CTGCGTATTG TGTATACCAT
     GGATTAGTCA
2251 AACGCACTAC AGGTATGTAG TAATGGATGA ATACACCGCT
     GGTGGATACA
2301 TAACTTGCTG GTATCAAACA AATATTGTGG TGCCTGCAGA
     TGCACAGAGT
2351 GACTGTAAGA TCTTGTGTTT TGTGTCGGCA TGTAACGATT
     TCTCAGTTAG
2401 GATGCTCAAG GACACACCCT TTATAAAACA GGATAATTTC
     TTCCAAGGGC
2451 CCCCAGGAGA GGTGATGGAA AGAGCCGTTG CCCGCGTCGC
     TGATACCATT
2501 GGGAGCGGAC CAGTTAACTC GGAATCCATT CCAGCTCTAA
     CCGCCGCAGA
2551 GACAGGGCAC ACGTCACAAG TTGTACCATC AGACACAATG
     CAAACTAGGC
2601 ACGTGAAGAA TTATCATTCA AGGTCAGAGT CGACAGTGGA
     GAACTTCCTG
2651 TGCAGATCTG CATGCGTCTT CTACACCACA TACAAGAACC
     ATGGCTCTGA
2701 TGGCGACAAC TTCGCCTACT GGGTAATCAA CACACGGCAA
     GTTGCTCAAC
2751 TGCGTCGGAA GCTCGAAATG TTCACGTACG CAAGATTTGA
     TCTGGAGTTG
2801 ACCTTCGTGA TCACTAGCAC TCAGGAACAA CCCACCGTTA
     AAGGTCAAGA
2851 TACACCAGTG CTCACCCACC AAATAATGTA TGTACCTCCA
     GGTGGTCCAG
2901 TACCCACAAA GGTAAACAGC TACAGCTGGC AAACGTCCAC
     CAACCCAAGT
2951 GTGTTCTGGA CGGAAGGGAG CGCACCGCCT CGAATGTCGA
     TACTATTCAT
3001 TGGCATAGGC AACGCATACA GCATGTTCTA TGACGGGTGG
     GCCAGGTTTG
3051 ACAAGCAAGG GACATACGGC GTCCAAGCAC TAAACAACAT
     GGGGACACTA
3101 TATATGAGAC ATGTGAATGA TGGGGGTCCC GGTCCCATTG
     TGAGCACAGT
3151 ACGAATTTAC TTCAAGCCAA AGCACGTCAA AACGTGGGTC
     CCAAGACCGC
3201 CCAGACTATG TCAATACCAA AAGGCTGGCA ACGTGAATTT
     TGAACCCACT
3251 GGTGTGACTG AGGGTAGGAC AGATATAACA ACCATGAAAA
     CCACTGGCGC
3301 CTTCGGGCAG CAGTCTGGTG CCGTGTACGT TGGCAACTAT
     AGAGTGGTGA
3351 ATAGACATCT CGCAACGCGC GCGGACTGGC AAAACTGTGT
     GTGGGAAGAC
3401 TACAACAGAG ACCTTCTAGT GAGCACCACC ACTGCACATG
     GCTGCGACAC
3451 CATTGCCAGG TGCGATTGCA CAGCAGGAGT GTACTTCTGC
     GCCTCCAGAA
3501 ACAAGCACTA TCCAGTCACA TTTGAGGGGC CCGGTCTTGT
     GAAGGTTCAA
3551 GAGAGTGAGT ATTACCCGAA AAAGTACCAA TCCCATGTAC
     TGCTCGCAGC
```

```
3601 TGGATTTGCA GAGCCGGGTG ATTGTGGAGG GATTCTCAGA
     TGCCAACATG
3651 GGGTGATTGG CATAGTTACC GTGGGGGGGG AAGGTGTTGT
     TGGTTTTGCC
3701 GATGTAAGAG ACTTGTTGTG GCTGGAGGAC GATGCCATGG
     AGCAAGGAGT
3751 TAGGGATTAT GTGGAACAAC TCGGCAACTG CTTCGGCTCA
     GGATTCACCA
3801 ATCAAATTTG CGAACAGGTT ACCCTTCTAA AAGAGTCGTT
     AATTGGACAG
3851 GATTCTATCC TTGAGAAGTC TCTCAAGGCC CTCGTCAAGA
     TAGTATCAGC
3901 ACTCGTGATC GTGGTGAGAA ATCACGATGA CCTCATTACG
     GTCACCGCCA
3951 CACTGGCGTT AATAGGATGT ACCACCTCAC CATGGCGCTG
     GCTCAAGCAG
4001 AAAGTGTCTC AGTACTATGG CATCCCCATG GCTGAAAGGC
     AAAATAGTGG
4051 CTGGTTAAAG AAGTTCACAG AGATGACCAA TGCCTGTAAG
     GGCATGGAGT
4101 GGATAGCCAT CAAGATCCAA AAATTCATAG AGTGGTTGAA
     GGTTAAGATC
4151 CTGCCAGAAG TCAAGGAAAA GCATGAGTTC CTCAACAGGC
     TTAAACAACT
4201 ACCACTCTTG GAAAGTCAAA TAGCAACTAT TGAGCAGAGT
     GCACCATCTC
4251 AAAGTGACCA GGAGCAACTA TTCTCTAATG TACAGTACTT
     TGCCCACTAC
4301 TGTCGGAAGT ATGCACCATT GTACGCCGCT GAAGCAAAGA
     GAGTGTTCTC
4351 ACTTGAAAAG AAGATGAGCA ATTACATACA GTTCAAGTCC
     AAATGCCGTA
4401 TTGAACCCGT CTGTCTCTTG CTCCATGGCA GCCCAGGCGC
     TGGGAAGTCT
4451 GTGGCAACGA ACTTGATTGG GCGCTCGCTC GCTGAGAAAC
     TCAACAGCTC
4501 GGTGTACTCA CTACCACCAG ATCCAGACCA TTTCGATGGT
     TACAAACAGC
4551 AAGCTGTTGT CATCATGGAC GACTTGTGCC AGAACCCGGA
     CGGTAAAGAT
4601 GTGTCCTTGT TCTGTCAGAT GGTCTCCAGC GTTGACTTCG
     TGCCTCCCAT
4651 GGCGGCGCTT GAGGAAAAAG GCATTCTATT CACCTCGCCG
     TTCGTTCTCG
4701 CGTCCACCAA TGCAGGGTCA GTTAACGCCC CCACGGTCTC
     CGACAGTAGA
4751 GCACTCGTAA GAAGGTTCCA TTTTGACATG AACATCGAGG
     TTATTTCCAT
4801 GTATAGCCAG AACGGTAAGA TCAACATGCC TATGGCAGTT
     AAAACATGTG
4851 ATGAGGAGTG TTGCCCGGTC AACTTCAAAA AGTGCTGCCC
     ACTAGTGTGT
4901 GGCAAAGCTA TACAATTCAT AGACAGGAGG ACCCAAGTTA
     GGTATTCATT
4951 GGACATGCTG GTTACCGAAA TGTTTAGGGA GTACAATCAC
     ACACACAGTC
5001 TGGGGGCCAC CCTCGAGGCA TTGTTCCAAG GACCACCAGT
     TTATAGAGAG
5051 ATCAAAATCA GTGTTGCCCC AGAAACTCCT CCACCACCAG
     CAGTTGCCGA
5101 CTTACTAAAA TCAGTAGACA GTGAGGCTGT GAGGGAGTAC
     TGCAAGGAGA
5151 AAGGGTGGCT TATACCAGAG GTCGATTCCA CCCTACAGAT
     AGAAAAGCAT
5201 GTGAGCAGAG CGTTCATATG TTTGCAAGCT CTAACCACAT
     TTGTCTCGGT
5251 TGCAGGCATA ATATACATCA TCTACAAATT GTTTGCAGGT
     TTCCAAGGCG
5301 CATACACAGG GATGCCTAAT CAGAAGCCCA AGGTGCCCAC
     CCTGAGACAA
5351 GCCAAAGTGC AGGGTCCAGC GTTTGAGTTC GCCGTGGCGA
     TGATGAAAAG
5401 AAACGCCAGT ACAGTGAAAA CTGAGTATGG TGAATTCACC
     ATGCTTGGGA
5451 TTTACGACAG GTGGGCGGTG TTGCCACGCC ATGCCAAACC
     TGGCCCCACC
5501 ATCTTGATGA ACGACCAGGT AGTCGGAGTG TTGGACGCCA
     AGGAACTAGT
5551 TGATAAAGAT GGGACCAACC TGGAATTGAC TCTCTTGAAG
     CTCAACCGCA
```

-continued

```
5601 ACGAGAAGTT TAGAGACATC AGGGGATTCT TAGCACGAGA
     GGAGGTCGAA
5651 GTGAACGAAG CTGTCCTAGC AATAAACACA AGTAAATTCC
     CGAATATGTA
5701 CATACCCGTG GGCCGGGTAA CCGACTATGG GTTCTTAAAT
     CTGGGTGGAA
5751 CCCCCACGAA GAGAATGCTC ATGTACAATT TCCCAACTAG
     GGCAGGCCAG
5801 TGTGGGGGTG TCCTTATGTC AACAGGGAAA GTCCTGGGAA
     TACATGTAGG
5851 AGGGAATGGA CACCAAGGGT TTTCAGCGGC ACTCCTCAGA
     CACTACTTCA
5901 ATGAGGAGCA GGGTGAGATA GAATTCATTG AGAGCTCAAA
     GGACGCAGGA
5951 TTTCCCGTGA TCAACACTCC CAGCAAGACA AAATTGGAAC
     CAAGTGTGTT
6001 TCACCACGTG TTCGAGGGCA ACAAGGAACC AGCGGTTCTC
     AGAAATGGGG
6051 ACCCACGACT CAAGGCCAAC TTTGAGGAGG CAATCTTCTC
     CAAGTACATT
6101 GGCAATGTTA ACACACATGT AGACGAGTAC ATGATGGAGG
     CTGTAGATCA
6151 TTATGCAGGA CAACTAGCCA CACTGGACAT CAGCACGGAA
     CCCATGAAGC
6201 TAGAAGATGC CGTGTATGGC ACTGAGGGGC TCGAAGCACT
     AGACCTGACC
6251 ACCAGTGCAG GTTACCCTTA TGTGGCCCTG GGTATCAAGA
     AAAGAGACAT
6301 CCTATCCAAG AAGACCAGAG ACCTTACCAA GCTAAAGGAA
     TGCATGGACA
6351 AATATGGTCT AAACTTGCCA ATGGTAACCT ATGTCAAGGA
     CGAGTTGAGA
6401 TCTGCCGACA AAGTGGCCAA GGGAAAATCC AGGCTCATCG
     AGGCTTCTAG
6451 CCTCAACGAC TCAGTAGCAA TGAGGCAGAC ATTTGGAAAC
     CTATATAAGA
6501 CTTTCCACCT CAACCCGGGC ATCGTTACGG GTAGCGCCGT
     TGGGTGTGAC
6551 CCAGATGTCT TTTGGAGCAA GATCCCCGTT ATGCTCGATG
     GACATGTCAT
6601 AGCGTTTGAC TATTCAGGCT ATGACGCCAG CCTCAGCCCA
     GTGTGGTTTA
6651 CGTGCTTGAA ACTCCTCCTG GAGAAGCTAG GGTACACAAA
     CAAGGAAACG
6701 AACTACATAG ACTACCTCTG TAATTCCCAC CACCTGTACA
     GGGACAAACA
6751 CTACTTTGTG AGGGGCGGCA TGCCATCAGG ATGCTCAGGC
     ACTAGCATAT
6801 TTAATTCCAT GATTAACAAC ATCATAATCA GAACCCTCAT
     GCTGAAGGTT
6851 TATAAAGGCA TTGATTTGGA CCAATTCAGA ATGATTGCAT
     ATGGGGATGA
6901 TGTGATAGCT TCATACCCGT GGCCCATCGA TGCCTCACTG
     CTAGCTGAAG
6951 CAGGGAAGGA TTGTGGCTTG ATCATGACCC CAGCAGATAA
     AGGCGAGTGT
7001 TTCAATGAGG TAACCTGGAC AAACATGACC TTCCTGAAAA
     GGTACTTCAG
7051 GGCAGATGAA CAGTACCCAT TTTTGGTCCA TCCTGTCATG
     CCAATGAAGG
7101 ATATACACGA ATCCATTAGG TGGACTAAAG ATCCTAAGAA
     CACACAGGAT
7151 CACGTGCGCT CGCTGTGTTT ATTGGCTTGG CACAACGGGG
     AGCACGAATA
7201 TGAGGAGTTT ATTCGTAAGA TCAGAAGCGT GCCCGTAGGG
     CGCTGCTTGT
7251 CCCTCCCTGC GTTTTCAACG CTGCGCAGGA AGTGGTTGGA
     CTCCTTTTAA
7301 AATTAGAGCA CAATTAGTCA ATCATAATTG GCTCAACCCT
     ACCGCATGAA
7351 CCGAACTTGA TAAAAGTGCG GTAGGGGTAA ATTCTCCGTA
     TTCGGTGCGG;
``` or a degenerate sequence which encodes the same amino acid sequence as SEQ ID NO: 1.

2. An isolated DNA molecule encoding a mutant strain of SVDV, comprising a sequence of SEQ ID NO: 1 with the bases at positions 2705–2710 replaced with GAAAGC (SEQ ID NO: 5), or a degenerate sequence which encodes the same amino acid sequence.

3. An isolated DNA molecule encoding a mutant strain of SVDV, comprising a sequence of SEQ ID NO: 1 with the bases at positions 2693–2710 replaced with GACAACG-GCGCTGAAAGC (SEQ ID NO: 6), or a degenerate sequence which encodes the same amino acid sequence.

4. An isolated DNA molecule encoding a mutant strain of SVDV, comprising a sequence of SEQ ID NO: 1 with the bases at positions 2693–2710 replaced with GGCTCCAC-CACAAACAAGGATAAGAGC (SEQ ID NO: 7), or a degenerate sequence which encodes the same amino acid sequence.

5. An isolated DNA molecule encoding a mutant strain of SVDV, comprising a sequence of SEQ ID NO: 1 with a substituted base at one or more of positions 2693–2710.

6. A mutant strain of SVDV, comprising a genome encoded by a DNA molecule comprising a sequence of SEQ, ID NO: 1 with a substituted base at one or more of positions 2693–2710.

7. A mutant strain of SVDV, comprising a genome encoded by a DNA molecule comprising a sequence of SEQ ID NO: 1 with the bases at positions 2705–2710 replaced with GAAAGC (SEQ ID NO: 5), or a degenerate sequence which encodes the same amino acid sequence.

8. A mutant strain of SVDV, comprising a genome encoded by a DNA molecule comprising a sequence of SEQ ID NO: 1 with the bases at positions 2693–2710 replaced with GACAACGGCGCTGAAAGC (SEQ ID NO: 6), or a degenerate sequence which encodes the same amino acid sequence.

9. A mutant strain of SVDV, comprising a genome encoded by a DNA molecule comprising a sequence of SEQ ID NO: 1 with the bases at positions 2693–2710 replaced with GGCTCCACCACAAACAAGGATAAGAGC (SEQ ID NO: 7), or a degenerate sequence which encodes the same amino acid sequence.

10. An expression plasmid comprising a sequence of SEQ ID NO: 1, or a degenerate sequence which encodes the same amino acid sequence as SEQ ID NO: 1.

11. The expression plasmid of claim 10, comprising expression plasmid pCI/SVDV-T deposited on Aug. 4, 1998, with China Center for Type Culture Collection, Luo Jia Shan, Wuhan, the People's Republic of China, under Accession No. CCTCC M 98013.

12. An expression plasmid comprising a sequence of SEQ ID NO: 1 with a substituted base at one or more of positions 2693–2710.

13. An expression plasmid comprising a sequence of SEQ ID NO: 1 that has been mutagenized at one or more bases encoding an amino acid at position 83, 84, 85, 86, 87, or 88 of the capsid protein VP1 (nucleotide position 2693–2710).

14. An expression plasmid comprising pCI/SVDV-T/SP7 deposited on Aug. 4, 1998, with China Center for Type Culture Collection, Luo Jia Shan, Wuhan, the People's Republic of China, under Accession No. CCTCC M 98012.

15. An expression plasmid comprising pCI/SVDV-T/H21 deposited on Aug. 4, 1998, with China Center for Type Culture Collection, Luo Jia Shan, Wuhan, The People's Republic of China, under Accession No. CCTCC M 98011.

16. An expression plasmid comprising pCI/SVDV-T/N3 deposited on Aug. 4, 1998, with China Center for Type Culture Collection, Luo Jia Shan, Wuhan, the People's Republic of China, under Accession No. CCTCC M 98010.

17. An immunogenic composition for use in prophylaxis of the SVDV, comprising the Taiwan Yu-Li strain of SVDV and an adjuvant for the composition.

18. An immunogenic composition for use in prophylaxis of the SVDV, comprising an adjuvant and a mutant strain of SVDV, the mutant strain comprising a genome encoded by a DNA molecule comprising a sequence of SEQ ID NO: 1 with a substituted base at one or more of positions 2693–2710.

19. An immunogenic composition for use in prophylaxis of the SVDV, comprising an adjuvant and a mutant strain of SVDV, the mutant strain comprising a genome encoded by a DNA molecule comprising a sequence of SEQ ID NO: 1 with the bases at positions 2705–2710 replaced with GAAAGC (SEQ ID NO: 5), or a degenerate sequence which encodes the same amino acid sequence.

20. An immunogenic composition for use in prophylaxis of the SVDV, comprising an adjuvant and a mutant strain of SVDV, the mutant strain comprising a genome encoded by a DNA molecule comprising a sequence of SEQ ID NO: 1 with the bases at positions 2693–2710 replaced with GACAACGGCGCTGAAAGC (SEQ ID NO: 6), or a degenerate sequence which encodes the same amino acid sequence.

21. An immunogenic composition for use in prophylaxis of the SVDV, comprising an adjuvant and a mutant strain of SVDV, the mutant strain comprising a genome encoded by a DNA molecule comprising a sequence of SEQ ID NO: 1 with the bases at positions 2693–2710 replaced with GGCTCCACCACAAACAAGGATAAGAGC (SEQ ID NO: 7), or a degenerate sequence which encodes the same amino acid sequence.

22. A mutant strain of SVDV, wherein the mutant strain has been altered so that two or more amino acids in VP1 positions 83–88 are different from a wild-type strain.

23. The mutant strain of claim 22, wherein all of the amino acids in VP1 positions 83–88 are different from a wild-type strain.

24. The mutant strain of claim 22, wherein additional amino acids are inserted.

25. A mutant strain of SVDV, wherein the mutant strain has been altered so that two or more codons in the region corresponding to nucleotides 2693–2710 of SEQ ID NO 1 encode amino acids different from a wild-type strain.

26. The mutant strain of claim 25, wherein all of the codons in the region corresponding to nucleotides 2693–2710 of SEQ ID NO 1 encode amino acids different from a wild-type strain.

27. The mutant strain of claim 25, wherein additional codons are inserted.

28. An immunogenic composition for use in prophylaxis of the SVDV, comprising an adjuvant and the mutant SVDV of claim 22, 23, 24, 25, 26, or 27.

* * * * *

UNITED STATES PATENT AND TRADEMARK OFFICE
CERTIFICATE OF CORRECTION

PATENT NO.  : 6,200,576 B1
DATED       : March 13, 2001
INVENTOR(S) : Hwong et al.

It is certified that error appears in the above-identified patent and that said Letters Patent is hereby corrected as shown below:

Title page,
Item [56], References Cited,
U.S. PATENT DOCUMENTS, "5,478,745" should read -- 5,748,746 --
Please insert -- FOREIGN PATENT DOCUMENTS 86105814  5/1/1997  (R.O.C.) --

Column 3,
Line 59, "32-34" should read -- 32 and 34 --

Column 4,
Line 37, please insert new paragraph beginning at "Accordingly"

Column 5,
Line 8, delete "m" before "differentiation"

Column 7,
Line 39, "109" should read -- $10^9$ --

Column 8,
Line 7, "10pi" should read -- 10μl --
Line 9, "pi" should read -- μl --
Line 20, "pi" should read -- μl --
Line 28, delete "d"

Column 9,
Line 21, "CO," should read -- $CO_2$ --

Column 10,
Line 32, "Bag" should read -- Eag --
Line 61, delete "25"

Column 11,
Line 15, move "[SEQ ID NO: 9]" down to end of sequence
Line 17, move "[SEQ ID NO: 10]" down to end of sequence
Line 21, move "[SEQ ID NO: 11]" down to end of sequence

UNITED STATES PATENT AND TRADEMARK OFFICE
CERTIFICATE OF CORRECTION

PATENT NO.    : 6,200,576 B1
DATED         : March 13, 2001
INVENTOR(S)   : Hwong et al.

It is certified that error appears in the above-identified patent and that said Letters Patent is hereby corrected as shown below:

Column 12
Line 60, move "[SEQ ID NO: 13]" down to end of sequence
Line 64, move "[SEQ ID NO: 14]" down to end of sequence Column 13,
Line 41, move "[SEQ ID NO: 15]" down to end of sequence
Line 45, move "[SEQ ID NO: 16]" down to end of sequence Column 16,
Line 9, "pi" should read -- µl --

Signed and Sealed this

Eighth Day of October, 2002

*Attest:*

JAMES E. ROGAN
*Director of the United States Patent and Trademark Office*

*Attesting Officer*